(12) United States Patent
Chen et al.

(10) Patent No.: US 8,993,007 B2
(45) Date of Patent: Mar. 31, 2015

(54) PREPARATION USED FOR ANTI-TACHYARRHYTHMIA AND ITS PREPARATION METHOD

(71) Applicant: Heshengyuan of Chinese Medicine Research & Development Company Limited in Shunde District of Foshan, Foshan, Guangdong (CN)

(72) Inventors: Keji Chen, Beijing (CN); Shouying Du, Beijing (CN); Xiaochang Ma, Beijing (CN)

(73) Assignee: Heshengyuan of Chinese Medicine Research & Development Company Limited in Shunde District of Foshan, Foshan, Guangdong (CN)

( * ) Notice: Subject to any disclaimer, the term of this patent is extended or adjusted under 35 U.S.C. 154(b) by 10 days.

(21) Appl. No.: 13/925,278

(22) Filed: Jun. 24, 2013

(65) Prior Publication Data
US 2013/0344175 A1  Dec. 26, 2013

Related U.S. Application Data

(63) Continuation-in-part of application No. PCT/CN2012/000867, filed on Jun. 25, 2012.

(51) Int. Cl.
*A61K 36/00* (2006.01)
*A61K 36/505* (2006.01)
*A61K 36/66* (2006.01)

(52) U.S. Cl.
CPC ............. *A61K 36/66* (2013.01); *A61K 36/505* (2013.01); *A61K 2236/39* (2013.01)
USPC ........................................................ 424/725

(58) Field of Classification Search
None
See application file for complete search history.

(56) References Cited

U.S. PATENT DOCUMENTS

2010/0021575 A1* 1/2010 Tang et al. .................... 424/778

OTHER PUBLICATIONS

Inserte et al., "Ischemic preconditioning prevents calpain-mediated impairment of Na+/K+-ATPase activity during early reperfusion," *Cardiovascular Research*, vol. 70, pp. 364-373, 2006.
Sun et al., "Intracellular calcium changes and tachycardia-induced contractile dysfunction in canine atrial myocytes," *Cardiovascular Research*, vol. 49, pp. 751-761, 2001.
Wu et al., "Angiotensin II does not influence expression of sarcoplasmic reticulum $Ca^{2+}$ ATPase in atrial myocytes," *Journal of the Renin-Angiotensin-Aldosterone System*, vol. 10, No. 3, pp. 121-126, Sep. 2009.
Zaugg et al., "When Calcium Turns Arrhythmogenic: Intracellular Calcium Handling during the Development of Hypertrophy and Heart Failure," *Croatian Medical Journal*, vol. 42, No. 1, pp. 24-32, 2001.
Sedej et al., "$NA^{+-dependent\ SR\ Ca2+}$ overload induces arrhythmogenic events in mouse cardiomyocytes with a human CPVT mutation," *Cardiovascular Research*, vol. 87, pp. 50-59, 2010.
Leszek et al., "Alteration of myocardial sarcoplasmic reticulum $Ca^{2+\ -ATPase\ and\ Na+\ -Ca2+}$ exchanger expression in human left ventricular volume overload," *European Journal of Heart Failure*, vol. 9, pp. 579-586, 2007.
Lampe et al., "Phosphorylation of Connexin43 on Serine368 by Protein Kinase C Regulates Gap Junctional Communication," *The Journal of Cell Biology*, vol. 149, No. 7, pp. 1503-1512, Jun. 26, 2000.
Bao et al., "Regulation of Purified and Reconstituted Connexin 43 Hemichannels by Protein Kinase C-mediated Phosphorylation of Serine 368," *The Journal of Biological Chemistry*, vol. 279, No. 19, pp. 20058-20066, May 7, 2004.
Turner et al., "Reversible Connexin 43 Dephosphorylation During Hypoxia and Reoxygenation Is Linked to Cellular ATP Levels," *Circulation Research*, vol. 95, pp. 726-733, Sep. 9, 2004.
Beardslee et al., "Dephosphorylation and Intracellular Redistribution of Ventricular Connexin43 During Eletrical Uncoupling Induced by Ischemia," *Circulation Research*, vol. 87, pp. 656-662, 2000.
Schulz et al., "Connexin 43 and ischemic preconditioning," *Cardiovascular Research*, vol. 62, pp. 335-344, 2004.
Solan et al., "Connexin phosphorylation as a regulatory event linked to gap junction channel assembly," *Biochimica et Biophysica Acta*, vol. 1711, pp. 154-163, 2005.
Moreno et al., "Gap junction channel gating modulated through protein phosphorylation," *Prog. Biophys. Mol. Biol.*, vol. 94, Nos. 1-2, pp. 107-119, 2007.

* cited by examiner

*Primary Examiner* — Qiuwen Mi
(74) *Attorney, Agent, or Firm* — Oliff PLC

(57) ABSTRACT

A kind of Corydalis extract for anti-tachyarrhythmia, the extract prepared by the following method: Corydalis crude powder 100 parts by weight, is extracted by 60-80% ethanol 600-1000 parts by volume in 1-3 times, combined filtrate, concentrated under reduced pressure to a fluidextract of the relative density of 0.2-0.5 g/mL; take the processed D101 resin, and the fluidextract prepared through the resin column with the flow rate of 0.2-0.5 mL/min, impurity of deionized water with the flow rate of 0.2-0.5 mL/min, 60-90% ethanol elution, flow rate 0.4-0.8 mL/min, and recover ethanol, concentrate to Corydalis extract dry paste. According to the conventional method of adding conventional accessories, made into clinically acceptable pills, capsules, granules, tablets, oral liquid or injection. The extract has obvious effect on anti-arrhythmia.

11 Claims, 11 Drawing Sheets

Drawings

PREPARATION USED FOR ANTI-TACHYARRHYTHMIA AND ITS PREPARATION METHOD

This is a Continuation-in-Part of International Application No. PCT/CN2012/000867 filed Jun. 25, 2012. The disclosure of the prior application is hereby incorporated by reference herein in its entirety.

TECHNICAL FIELD

The invention relates to a traditional Chinese medicine and its preparation method, and more particularly a preparation used for anti-tachyarrhythmia and its preparation method.

THE TECHNICAL BACKGROUND

Tachyarrhythmias in acute myocardial infarction (acute myocardial infarction, AMI) acute phase is one major cause of death. Although thrombolytic or interventional therapy for myocardial salvage dying or improving myocardial blood supply is valid, but its complications arrhythmia can not obtain satisfactory results. For the vast majority of arrhythmia, drug therapy is the foundation and the preferred method of treatment, the clinical drug commonly used has some side effects and limitations of treatment, therefore, the research and development of fast, safe and reliable new drug with the unique role of anti-tachyarrhythmia is very necessary.

THE CONTENT OF THE INVENTION

The object of the present invention is to provide an anti-tachyarrhythmia preparation and its preparation method.

The present invention aims to achieve through the following technical solutions:

One kinds of Corydalis extract, corydalis crude powder 100 parts by weight, is extracted by 60-80% ethanol 600-1000 parts by volume in 1-3 times, combined filtrate, concentrated under reduced pressure to a fluidextract of the relative density of 0.2-0.5 g/mL; take the processed D101 resin, and the fluidextract prepared through the resin column with the flow rate of 0.2-0.5 mL/min, impurity of deionized water with the flow rate of 0.2-0.5 mL/min, 60-90% ethanol elution, flow rate 0.4-0.8 mL/min, and concentrate to Corydalis extract dry paste.

The present invention is preferably the following technical solution

Corydalis crude powder 100 parts by weight, is extracted by 70% ethanol 800 parts by volume in 2 times, combined filtrate, concentrated under reduced pressure to a fluidextract of the relative density of 0.3 g/mL; take the D101 resin processed, and the fluidextract prepared through the resin column with the flow rate of 0.4 mL/min, impurity of deionized water with the flow rate of 0.4 mL/min, 80% ethanol elution 8 times volume, flow rate 0.6 mL/min, and concentrate to Corydalis extract dry paste.

According to a conventional method to add the conventional excipients, corydalis dry extract made clinically acceptable dosage form including, but not limited to, pills, capsules, granules, tablets, oral liquid preparations or injections, etc.

D101 macroporous resin of the present invention, the ratio of diameter and height of D101 macroporous resin is 1:4-8; the sample solution of fluidextracts is adjusted to pH 1-2, and the precipitate is dissolved and scattered. Preferably D101 macroporous resin, the ratio of diameter and height of D101 macroporous resin is 1:7, the sample solution of fluidextracts is adjusted pH 1.5. The invention of the weight and volume relationship is for g/ml relationship.

Corydalis is commonly used in traditional Chinese medicine, it is warm, bitter acrid taste, into the heart, liver, spleen, lung, with activating blood circulation, regulating qi, and analgesic effect, can cure all kinds of pain, used in the treatment of pectoral stuffiness pain and acute epigastralgia. Corydalis as single herb screened from a prescription achieved a positive effect in the early trials of the invention. According to polar differences of Corydalis extract, the present invention is prepared to water extracts, alcohol extracts, the organic phase and the aqueous phase portion of alkaloids extracted parts, macroporous resin enrichment parts, the original medicinal powder, the seven different medical screened parts from Tetrahydropalmatine's raw materials used for medical screening tests. Preferably the location with the best efficacy is for purification.

EXPERIMENTAL EXAMPLE 1

Preparation of Medical Screened Parts

1 Instruments and Materials 1.1 Instruments

Figure 1:
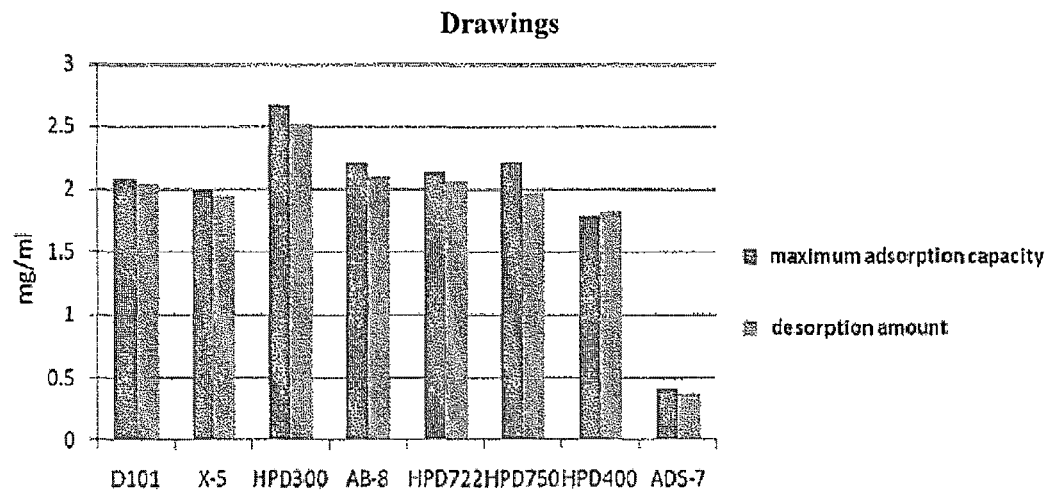
FIG. 1 Comparison of macroporous resin for Bamatin's maximum static adsorption and desorption amount effect.
Figure 2:
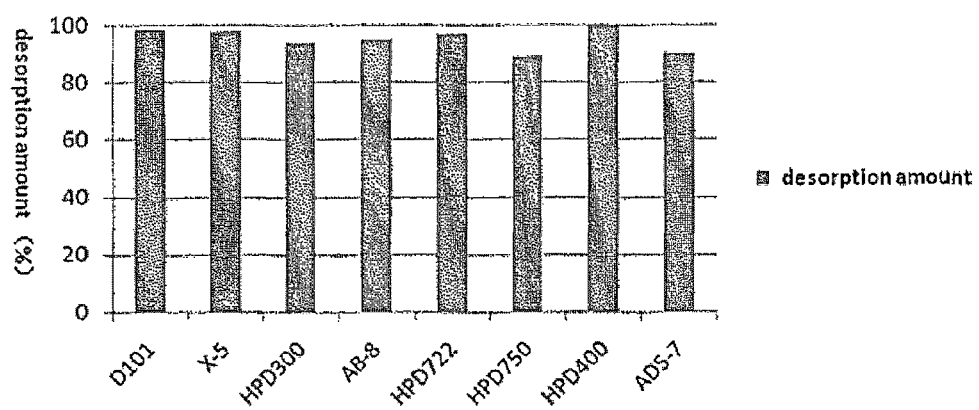
FIG. 2 Comparison of macroporous resin for Bamatin's static desorption rate effect.
Figure 3:
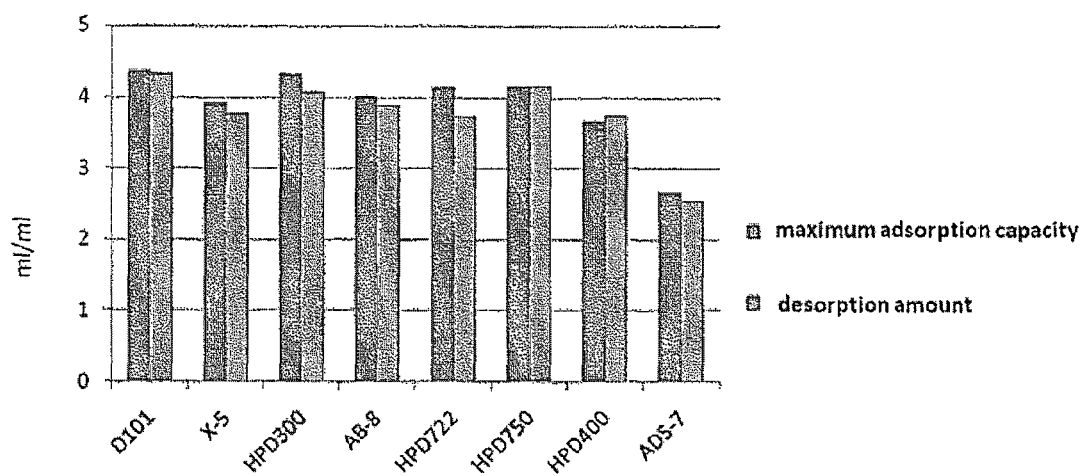
FIG. 3 Comparison of macroporous resin for tetrahydropalmatine's maximum static adsorption and desorption amount effect.
Figure 4:
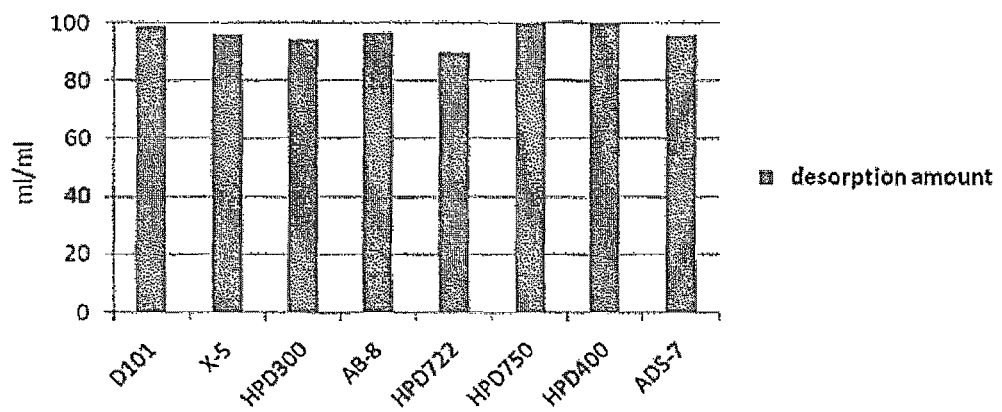
FIG. 4 Comparison of macroporous resin for tetrahydropalmatine's static analysis effect.
Figure 5:
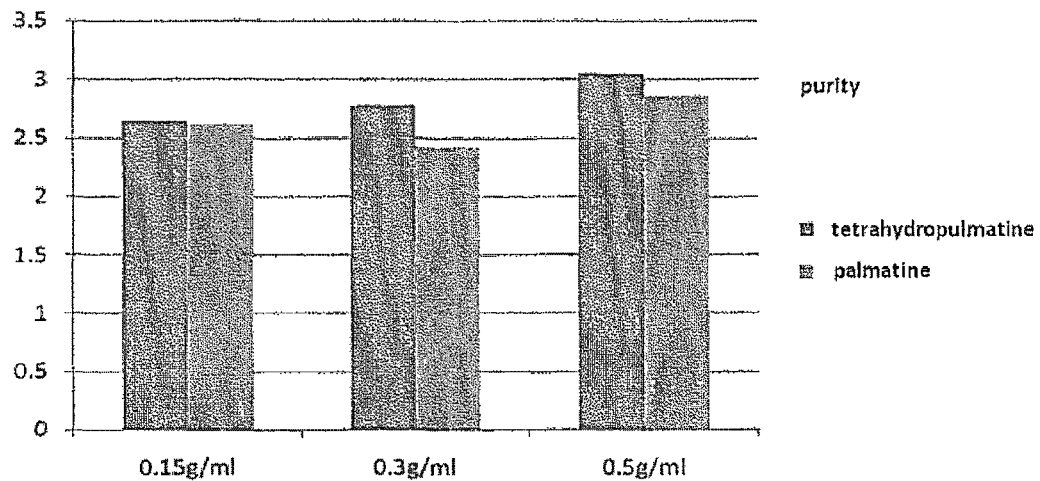
FIG. 5 Comparison of the purity of the two components through the resin column in the sample solution of different concentration.
Figure 6:
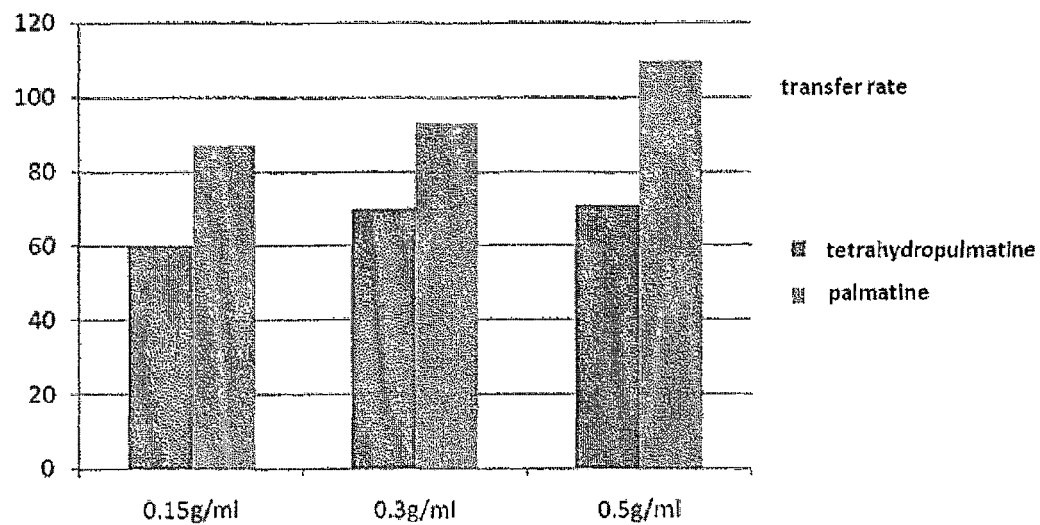
FIG. 6 Comparison of the transfer rate of the two components through the resin column of the sample solution of different concentration.

LC-20AT high performance liquid chromatograph (SPD-20AVWD detector, quaternionic low pressure gradient pump, column incubator, autosampler; Shimadzu Corporation of Japan, LCSolution chromatography workstation); Dikma Diamonsil C18 column (4.6 mm×250 mm, 5 μm; column number: 8132893); METTLER AE 240 type electronic analytical balance (Mettler Toledo Instrument Co., Shanghai company); Sartorius BS 110S electronic analytical balance (Beijing sartorius Scientific Instrument Co. Ltd.); YP10002 type electronic balance (Shanghai Yueping Scientific Instrument Co., Ltd).

1.2 Material 101 macroporous resin (Cangzhou bao-en Adsorbent Technology Ltd, pharmaceutical grade); Tetrahydropahnatine (Zhengzhou Linuo Biological Technology Co., Ltd.)

1.2.1 Reagent

Ethanol (Beijing chemical plant Analytical grade), chloroform (Beijing chemical plant Analytical grade), hydrochloric acid (Beijing chemical plant Analytical grade), ammonia (Shantou Xilong Chemical Co., Ltd. Analytical grade)

1.2.2 Control

Tetrahydropalmatine control (batch number: 110726-200409) purchased from China pharmaceutical biological products analysis institute, for the determination of use 2 Methods and Results 2.1 Preparation of Alcohol Extracts (Sample No. 5)

Corydalis crude powder 100 g, is extracted by 80% ethanol 800 ml for 2 times, combined filtrate, concentrated under reduced pressure to obtain fluidextract 120 mL and dried to give a solid alcohol extract.

2.2 The Products Enriched by D101 Resin (Sample No. 1)

Handled D101 resin 10 mL is loaded into a glass column of 1.0 cm inner diameter, washed with water until no alcohol flavor, taked the fluidextract 6.0 mL prepared by the method 2.1 through the resin column, flow rate 3.5 mL/h, removed impurities by deionized water, flow rate 3.5 mL/h, eluted with 36 mL by 80% ethanol, flow rate of 3 mL/min, concentrated to a dry paste, as macroporous resin enriched products.

2.3 Preparation of the Fat-Soluble and the Soluble Alkaloid Extracts (Sample No. 2, No. 3)

Corydalis crude powder 200 g, is extracted by 80% ethanol 1600 ml two times, refluxed for 1.5 h, filtered to obtain the filtrate, concentrated under reduced pressure into a thick paste about 200 mL, adjusted with hydrochloric acid of 1.0 mol/L to pH=1, standed 24 h at 5□, filtered and washed precipitate, the filtrate was added water to 400 mL, adjusted with ammonia water to pH=10, adjusted to 500 mL total liquid finally, extracted twice with methylene chloride (300 mL×2) and combined the organic phases, recovered the solvent under reduced pressure to the fat-soluble alkaloids (Sample No. 3); the aqueous phase after extraction, is concentrated, and dried to the water-soluble alkaloids (Sample No. 2).

2.4 Preparation of Water Extracts (Sample No. 4)

Figure 18:
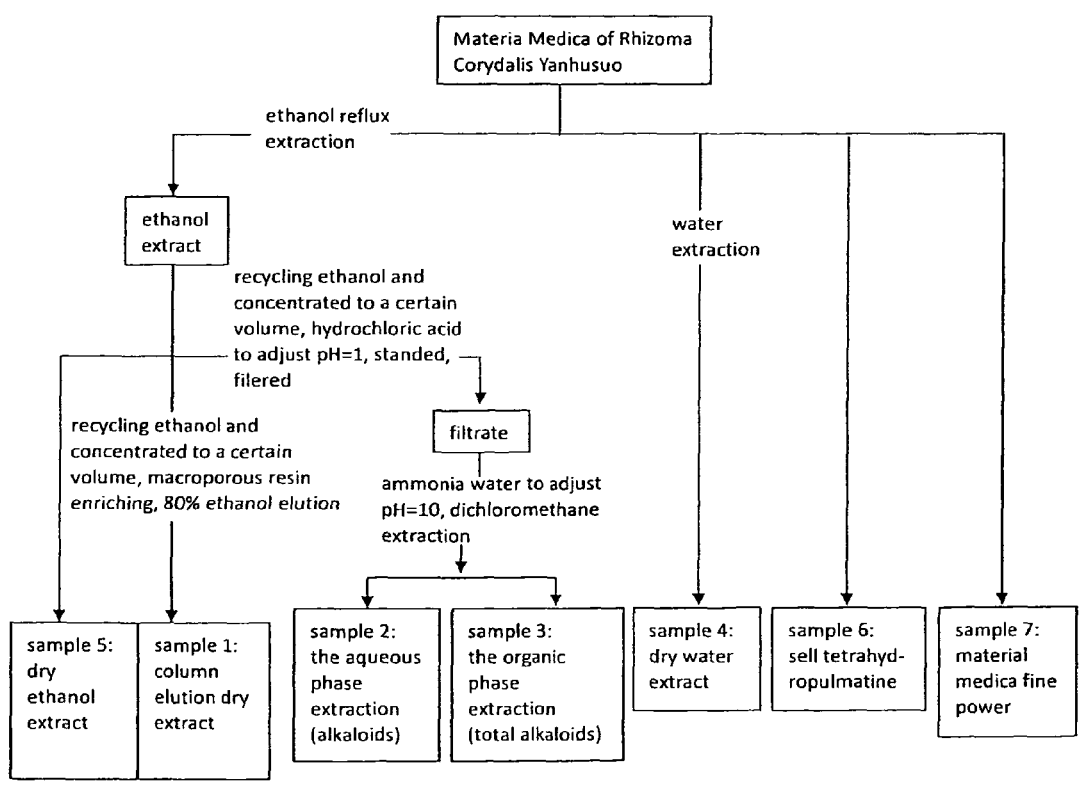
FIG. 18 The schematic diagram of the preparation of medicine screened portion.

Corydalis crude powder 100 g, boiled with water 800 mL for 1.5 h two times. With gauze filtration, the filtrate was concentrated to 400 mL, and dried to obtain dry extract as water extract portion. The Preparation of Corydalis herbs screening portion shown in FIG. 18.

TABLE 1

| | Efficacy screening test drug group | |
|---|---|---|
| Code | Name | The content of Tetrahydropalmatine |
| NO. 1 | The D101 column elution | 4.25% |
| NO. 2 | Aqueous phase (Water Soluble Alkaloids part) | 0 |
| NO. 3 | Organic phase (Fat-Soluble Alkaloid part) | 11.18% |
| NO. 4 | Dry water extract | 0.204% |
| NO. 5 | Dry ethanol extract | 7.30% |
| NO. 6 | Tetrahydropalmatine API | 92.3% |
| NO. 7 | *Corydalis* powder | 0.12% |

EXPERIMENTAL EXAMPLE 2

Efficacy Screening Test (the Same Samples as in Experimental Example 1)

1 Experimental Materials 1.1 Experimental Animal

90 CD mice, male, weighing 28-30 g, Beijing Vital River Laboratory Animal Technology Co., license number Sea (Beijing) 2006-0009.

1.2 Drugs 1.3 Reagents $FeCl_3 \cdot 6H_2O$ (Beijing Chemical Factory, A.R.), Triphenyltetrazolium chloride (Beijing Chemical Factory A.R. batch number: 950221).

1.4 Instruments

TT stereomicroscope (Beijing electric scientific instrument factory), SHZ-22 Constant temperature water bath oscillator (Jiangsu Okura medical instrument factory), Electronic analytical balance (SHIMADZU, AEG-220).

2 Experimental Methods 2.1 Experimental Groups

Animals were randomly divided into 9 groups, with 10 rats in each group: model group (physiological saline 10 mL/kg), the control drug amiodarone group 78 mg/kg, NO. 1 drug group 18.2 mg/kg, NO. 2 drug group 157.6 mg/kg, NO. 3 drug group 9.1 mg/kg, NO. 4 drug group 462 mg/kg, NO. 5 drug group 139 mg/kg, NO. 6 drug group 1.16 mg/kg, NO. 7 drug group 1.3 g/kg. Before administration each drug was prepared to the desired concentration with physiological saline, duodenal route of administration, the dose of 10 mL/kg.

2.2 Operation Method

Animal with sodium pentobarbital intraperitoneal anesthesia (60 mg/kg), open the peritoneal cavity, duodenal feeding physiological saline or drugs, suturing; administered 45 minutes later, connecting physiological recorder (PowerLab) records standard lead II ECG, tail vein injection of $CaCl_2$ (180 m/kg, 10 mg/mL, finishing in 10 seconds and injecting in constant speed), observed whether induced electrocardiogram of arrhythmia, recorded the arrhythmia duration; and the results were statistically analyzed.

2.3 Score Standard and Test Results

Observed ECG whether induced arrhythmia, recorded the duration of ventricular arrhythmia; and the results were statistically analyzed. The statistical results are shown in table 2:

TABLE 2

Efficacy results of the screening

| | | | | Duration/s | | | | |
|---|---|---|---|---|---|---|---|---|
| Code | Model group | amiodarone | Sample1 | Sample2 | Sample3 | Sample4 | Sample5 | Sample6 | Sample7 |
| 1 | 62 | 0 | 108 | 103 | 95 | 110 | 226 | 79 | 155 |
| 2 | 164 | 86 | 110 | 54 | 140 | 110 | 100 | 130 | 190 |
| 3 | 161 | 88 | 40 | 82 | 56 | 130 | 89 | 80 | 195 |
| 4 | 123 | 120 | 65 | 83 | 20 | 140 | 180 | 70 | 92 |
| 5 | 130 | 60 | 110 | 71 | 165 | 55 | 130 | 70 | 220 |
| 6 | 105 | 106 | 120 | 63 | 57 | 92 | 190 | 79 | 60 |
| 7 | 120 | 76 | 52 | 80 | 114 | 73 | 86 | 100 | 76 |
| 8 | 74 | 53 | 75 | 82 | 119 | 77 | 139 | 47 | 101 |
| 9 | 96 | 104 | 87 | 165 | 130 | 202 | 189 | 181 | 150 |
| 10 | 196 | 99 | 120 | 57 | 33 | 90 | 120 | 104 | 102 |
| Mean | 123.1 | 79.2 | 88.7 | 84.0 | 92.9 | 107.9 | 144.9 | 94.0 | 134.1 |
| SD | 41.7 | 34.7 | 29.3 | 31.9 | 48.8 | 42.1 | 48.6 | 38.0 | 55.4 |
| t value | | 2.5565 | 2.1335 | 2.3520 | 1.4862 | 0.8110 | 1.0757 | 1.6297 | 0.5012 |

2.5 Conclusion

The model group as the negative control group, amiodarone group as the positive group, finally the group with shorter duration of arrhythmia is excellent. It can be seen from the results, samples 4, 5, 7 have poor or no pharmacodynamic effect; sample 3, 6 are medium, the efficacy of sample 1, 2 is close to the positive group. By pharmacodynamic results, Rhizoma Corydalis in both fat-soluble alkaloids and water-soluble alkaloids have a certain effect on the tachyarrhythmia, in the seven components, macroporous resin column elution composition not only contains fat-soluble alkaloid, also contains water-soluble alkaloids, with outstanding efficacy.

EXPERIMENTAL EXAMPLE 3

Separation and Purification of Rhizoma Corydalis by Macroporous Adsorption Resin 1 Instruments and Materials 1.1 Instruments LC-20AT high performance liquid chromatograph (SPD-20AVWD detector, quaternionic low pressure gradient pump, column incubator, autosampler; Shimadzu Corporation, LCSolution chromatography workstation); METTLER AE 240 type electronic analytical balance (Mettler Toledo Instrument Co., Ltd. Shanghai); Sartorius BS110S electronic analytical balance (Beijing sartorius Scientific Instrument Co., Ltd).

1.2 Material 1.2.1 Reagent

Methanol (Fisher Company, HPLC grade); acetonitrile (HPLC grade Mairui Da Company); phosphate (Tianjin Guangfu Fine Chemical Research Institute, HPLC grade); acetic acid (Fisher Company, HPLC grade); triethylamine (Tianjin Guangfu Fine Chemical Institute, AR); purified water (Hangzhou Wahaha Co.); sodium hydroxide (Tianjin Guangfu fine Chemical Research Institute, AR); hydrochloric acid (Beijing Chemical Factory, AR)

1.2.2 Control

Dehydrocorydaline (batch number: 042-30751 Wako Pure Chemical Industries, Ltd.);

Tetrahydropalmatine (batch number: 110726-201011 China Pharmaceutical and Biological Products, for the use of determination)

Hydrochloride, Martin (batch number: 732-9002 China Pharmaceutical and Biological Products, for the use of determination)

2 Screening of 2 Types of Macroporous Adsorption Resin

By static adsorption method, the most suitable macroporous adsorption resin was screened through the determination of the maximum adsorption capacity and desorption rate. The eight types of macroporous adsorption resin were selected, the specific data in table 3:

TABLE 3

The eight types of macroporous adsorption resin:

| Code | type | Polarity | specific surface area ($m^2/g$) | Average pore diameter (A °) | Factory |
|---|---|---|---|---|---|
| 1 | D101 | Non-polar | ≥400 | 100-110 | Bao En |
| 2 | HPD300 | Non-polar | 800-870 | 50-55 | Bao En |
| 3 | X-5 | Non-polar | 500~600 | 290~300 | Man Kai |
| 4 | AB-8 | Weakly polar | 480-520 | 130-140 | Bao En |
| 5 | HPD722 | Weakly polar | 485-530 | 130-140 | Bao En |
| 6 | HPD400 | Medium polar | 500-550 | 75-80 | Bao En |
| 7 | HPD750 | Medium polar | 650-700 | 85-90 | Bao En |
| 8 | ADS-7 | Polar | | | Bao En |

Each of the above processed resin 5 mL, is placed in the flask, removed surface moisture, added precisely Corydalis extract 200 mL that was concentrated to 0.3 g crude drug/mL, shaked, standed for 24 hours, sucking filtration, and washed the resin with distilled water 30 mL, combined filtrate and washed water and metered volume in 250 mL volumetric flask, shaked, Tetrahydropalmatine was measured by HPLC, calculated the maximum adsorption capacity. Two samples were processed parallelly.

The macroporous resin above washed with water was added 95% ethanol 200 mL, soaked 24 h, filtered, and washed with 30 mL of 95% ethanol, combined ethanol solution, metered volume in 250 mL volumetric flask, shaked, measured content HPLC, calculated resolution rate.

The maximum adsorption capacity=(The concentration of initial solution−The concentration after adsorpted)×The adsorption volume/The resin volume](mg/mL resin)

The resolution rate=(The eluent concentration×The eluent volume)/(The adsorption capacity×The resin volume)]×100%

TABLE 4

Comparison of static adsorption of the macroporous resin effect on Bamatin

| Resin type | Code | The maximum adsorption capacity (mg/mL) | The resolution rate(%) | The maximum adsorption capacity × The resolution rate |
|---|---|---|---|---|
| Non-polar | D101 | 2.0797 | 98.4748 | 2.0480 |
|  | X-5 | 1.9862 | 97.8411 | 1.9433 |
|  | HPD300 | 2.682 | 94.0186 | 2.5216 |
| Weakly polar | AB-8 | 2.2104 | 94.9575 | 2.0989 |
|  | HPD722 | 2.1297 | 96.9996 | 2.0658 |
| Medium polar | HPD750 | 2.2188 | 88.9986 | 1.9747 |
|  | HPD400 | 1.7822 | 102.3005 | 1.8232 |
| Polar | ADS-7 | 0.4087 | 90.3156 | 0.3691 |

From the experimental results, the adsorption of Quaternary alkaloid of the HPD300 is much higher than other types of resin adsorption, the adsorption capacity is also very high, but its resolution is behind in rank in these eight kinds of resin.

D101 resin for adsorption and desorption amount of quaternary ammonium alkaloid is not the biggest, but its resolution is higher.

TABLE 5

Comparison of static adsorption of the macroporous resin effect on Tetrahydropalmatine

| Resin type | Code | The maximum adsorption capacity (mg/mL) | The resolution rate(%) | The maximum adsorption capacity × The resolution rate |
|---|---|---|---|---|
| Non-polar | D101 | 4.3776 | 98.9378 | 4.3311 |
|  | X-5 | 3.9202 | 96.1614 | 3.7697 |
|  | HPD300 | 4.3214 | 94.2223 | 4.0718 |
| Weakly polar | AB-8 | 4.0115 | 96.72 | 3.88 |
|  | HPD722 | 4.1363 | 89.9138 | 3.7191 |
| Medium polar | HPD750 | 4.1496 | 100.093 | 4.1535 |
|  | HPD400 | 3.6653 | 101.9065 | 3.7351 |
| Polar | ADS-7 | 2.6578 | 95.9967 | 2.5514 |

From the experimental results, the adsorption of Tetrahydropalmatine of HPD300 is higher, analytical capacity and resolution is not high; The adsorption quantity of Tetrahydropalmatine, analytical capacity and resolution of D101 resin were all higher.

Considered from the adsorption, resolute quantity and resolution, HPD300 resin and D101 resin have their respective advantages, so in the following experiments, both resins were taken to comparative tests.

3 Investigation of the Concentration of Column Solution

A certain amount of the extracted liquid was concentrated to three concentrations of 0.15 g crude drug/mL, 0.3 g crude drug/mL, and 0.5 g crude drug/mL, and the volumes of 100 mL, 50 mL, and 30 mL, put into 10 mL macroporous resin column respectively, washed with water for three times of column volume, eluted with 95% ethanol for three times the column volume. The eluted liquid was taken into the liquid phase to determinate the related ingredient content, and calculate the transfer rate and purity. The results show in table 6:

TABLE 6

The results of the concentration of column solution

| | Transfer rate | | Purity | |
|---|---|---|---|---|
| Concentration | Tetrahydro-palmatine | Bamatin | Tetrahydro-palmatine | Bamatin |
| 0.15 g/mL | 63.26% | 87.67% | 2.83% | 2.63% |
| 0.3 g/mL | 69.83% | 92.97% | 2.77% | 2.42% |
| 0.5 g/mL | 66.30% | 94.03% | 2.77% | 2.51% |

Considering the transfer rate, purity and centrifugal precipitation, the concentration of 0.3 g/mL is chosen as the final concentration on the column solution.

4. Investigation of the pH of the Sample Solutions

The Corydalis alcohol extract was concentrated to 0.3 g crude drug/mL, regulated pH value in turn with concentrated hydrochloric acid to 6 (not regulated pH value), 5, 4, 3, and 1.5, ultrasonic treated for 20 minute in each of pH value, placed for 1 hour, observed the sedimentation dissolving condition. It was found that the precipitate can dissolve and does not form a block when the pH value in 1.5, thus determined the pH value of column solution is 1.5.

5. Pretreatment and Packing Column with Macroporous Adsorption Resin

The screening resin standby with 95% ethanol reflux liquid handling, and diluted with water not cloudy in the tube, the determination of ethanol reflux liquid absorption value of less than 0.1 UV spectrophotometry, the treated resin is arranged on the column before use rinsing with distilled water until the effluent liquid chromatographic column, using ethanol alcohol meter content measurement result is 0, spare. Parallel operation of two copies.

6. The Column Liquid Preparation

Weigh the coarse powder of Herba corydalis tuber, 8 times amount of 80% ethanol reflux extraction 2 times, each time 1 h, the extraction liquid is filtered, filtrate, vacuum concentration to 0.3 g crude drug/mL. It's determinated by HPLC to get the content of tetrahydropalmatine and Bamatin of the column liquid, spare.

Figure 7:
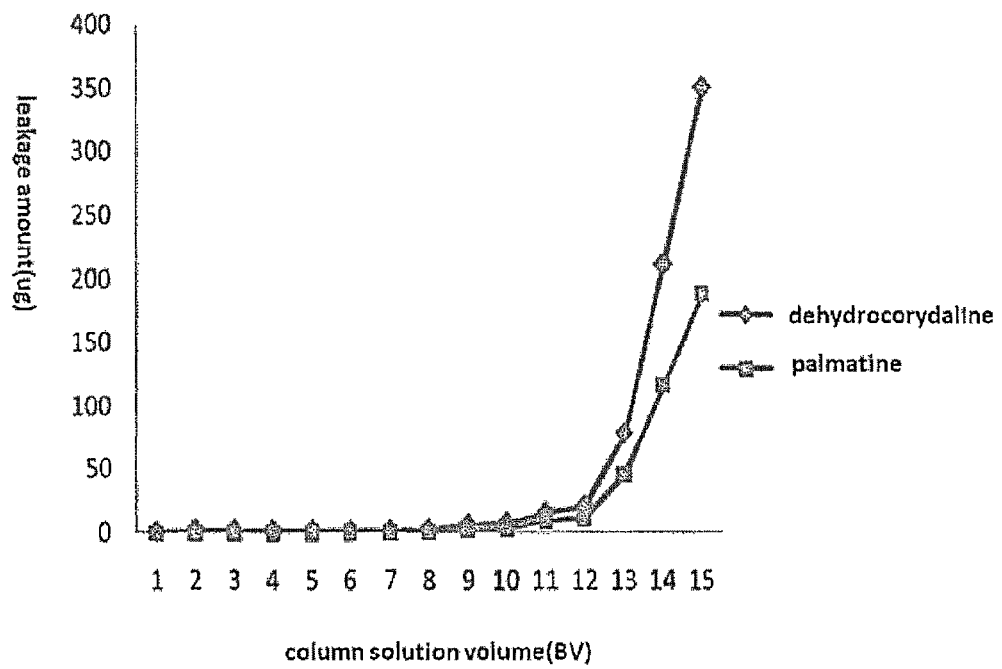
FIG. 7 HPD300 resin leaking curve.

7. Investigation of the Maximum Volume of the Sample Solutions 7.1 Investigation of the Maximum Volume of the HPD300 Resin 20 mL of HPD300 macroporous resin processed was packed in two chromatography columns, the sample solution of pH 1.5 was loaded with the flow rate of 0.4 mL/min, collected once every one column volume, and determinate the content of dehydrocorydaline, Bamatin, tetrahydropalmatine, render the leakage curves. The results show in FIG. 7:

TABLE 7

Investigation of the maximum volume of the HPD300 resin (n = 2)

| Multiples of the sample | The amount of leakage/ug | |
|---|---|---|
| | Dehydrocorydaline | Bamatin |
| 1 | 0.4117 | 0 |
| 2 | 1.2890 | 0 |
| 3 | 1.2576 | 0 |
| 4 | 1.4980 | 0 |
| 5 | 1.6046 | 0.2132 |
| 6 | 1.4731 | 0.2489 |
| 7 | 1.6860 | 0.1981 |
| 8 | 2.4267 | 0.7056 |
| 9 | 5.9836 | 2.4892 |
| 10 | 7.4632 | 3.6978 |
| 11 | 15.5734 | 8.7385 |
| 12 | 20.6402 | 11.7724 |
| 13 | 78.4829 | 45.6343 |
| 14 | 211.8286 | 116.2819 |
| 15 | 351.4834 | 188.1947 |

From the leakage curves, dehydrocorydaline began to leak from the seventh times column volume. For ensuring that the sample is not easy to leak, it was determinated the maximum sample volume is the 6 times of column volume, namely 1.8 g crude drug/mL resin.

Figure 8:
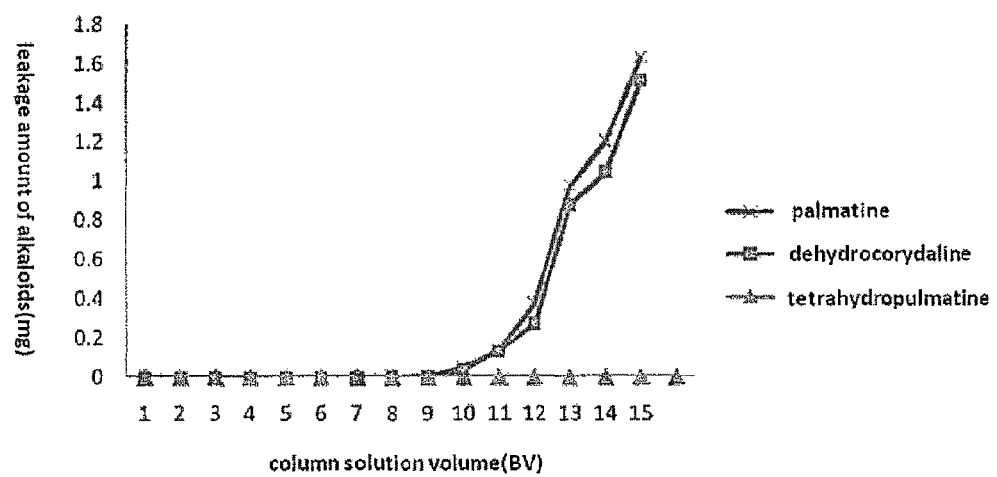
FIG. 8 D101 resin leaking curve.
Figure 9:
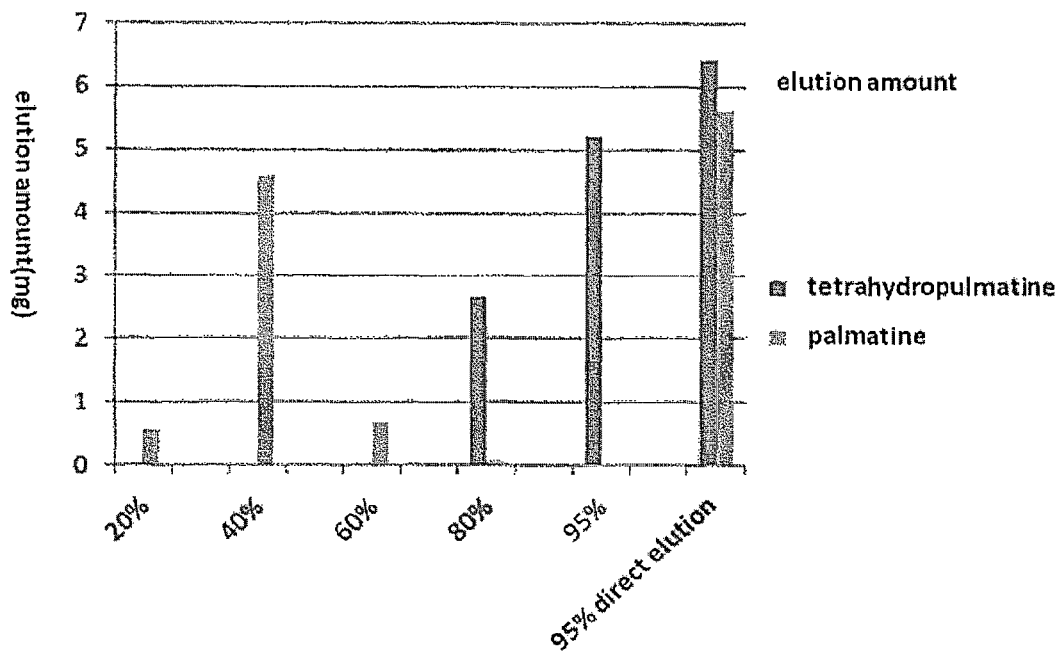
FIG. 9 Observation of the ethanol elution concentration of HPD300 resin-Comparison of the elution volume.
Figure 10:
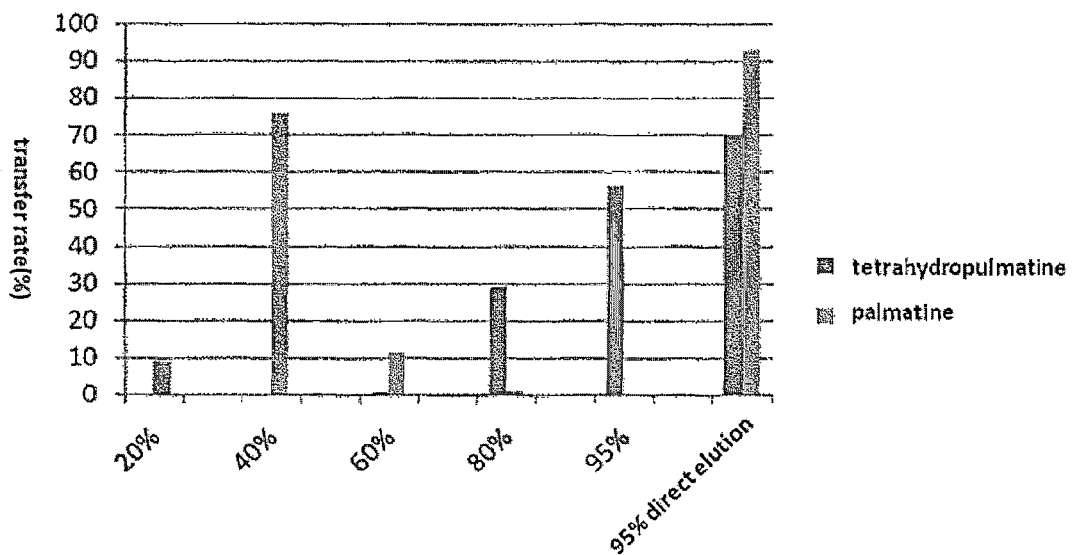
FIG. 10 Observation of the ethanol elution concentration of HPD300 resin-Comparison of the transfer rate.

7.2 Investigation of the Maximum Amount of the Sample 10 mL of D101 macroporous resin processed was packed in two chromatography columns 12 mmI.D.), the sample solution was loaded with the flow rate of 0.4 mL/min, collected once every one column volume, and determinate the content of dehydrocorydaline, Bamatin, and tetrahydropalmatine, render the leakage curves. The results show in Table 8 and FIG. 8

TABLE 8

Investigation of the maximum volume of the D101 resin (n = 2)

| The sample volume (BV) | The amount of leakage/ug | | |
|---|---|---|---|
| | Bamatin | Dehydrocorydaline | Tetrahydropalmatine |
| 1 | 0 | 0 | 0 |
| 2 | 0 | 0 | 0 |
| 3 | 0 | 0 | 0 |
| 4 | 0 | 0 | 0 |
| 5 | 0 | 0 | 0 |
| 6 | 0 | 0 | 0 |
| 7 | 0 | 0 | 0 |
| 8 | 0 | 0.001 | 0 |
| 9 | 0.008 | 0.005 | 0 |
| 10 | 0.053 | 0.037 | 0 |
| 11 | 0.133 | 0.129 | 0 |
| 12 | 0.373 | 0.269 | 0 |
| 13 | 0.974 | 0.878 | 0 |
| 14 | 1.201 | 1.043 | 0 |
| 15 | 1.625 | 1.512 | 0 |

From the leakage curves, Bamatin began to leak from the 9 times column volume.dehydrocorydaline began to leak from the 8 times column volume, tetrahydropalmatine has not been leaked. For ensuring that the sample is not easy to leak, it was determinated the maximum sample volume is the 7 times of column volume, namely 2.1 g crude drug/mL resin.

8. Investigation of the Flow Rate of the Sample Solutions 8.1 Investigation of the Flow Rate of the HPD300 Resin 10 mL of HPD300 macroporous resin processed was packed in the same type of chromatography columns, 60 mL of the sample solution was drew precisely, adsorbed dynamically with the flow rate of 0.4 mL/min, 0.6 mL/min, and 0.8 mL/min respectively, and measured the effluent results of the sample. The sample with the flow rate of 0.4 mL/min and 0.6 mL/min have not been leaked in 6 times column volumes, the sample with the flow rate of 0.8 mL/min began to leak from the 5 times column volume, so the final choice was the flow rate of 0.6 mL/min.

8.1 Investigation of the Flow Rate of the D101 Resin

HPD300 macroporous resin processed 10 mL was packed in two chromatography columns (12 mmI.D.), 70 mL of the sample solution was drew precisely, adsorbed dynamically with the flow rate of 0.4 mL/min, 0.6 mL/min, and 0.8 mL/min respectively, collected once every one column volume, and measured the effluent results of dehydrocorydaline, Bamatin, and tetrahydropalmatine in the sample, the sample with the flow rate of 0.4 mL/min have not been leaked, so the flow rate of 0.4 mL/min was chosen.

9 Investigation of the Concentration of Ethanol Elution 9.1 Investigation of the Concentration of Ethanol Elution by HPD300 Resin 10 mL of HPD300 macroporous resin processed was packed in two chromatography columns (12 mmI.D.), 60 mL of the sample solution was drew precisely, loaded dynamically with the flow rate of 0.6 mL/min, washed three column volumes (0.6 mL/min), washed successively with 20%, 40%, 60%, 80%, and 95% ethanol three column volumes of elution, the flow rate was 0.6 mL/min, the content and the paste volume of tetrahydropalmatine and Bamatin were measured in each alcohol elution to calculate elution rate and purity.

Additionally, 10 mL of HPD300 macroporous resin processed was packed in two chromatography columns (12 mmI.D.), 60 mL of the sample solution was drew precisely, loaded dynamically with the flow rate of 0.6 mL/min, washed three column volumes (0.6 mL/min), washed with 95% ethanol three column volumes of elution, the flow rate was 0.6 mL/min, the content and the paste volume of tetrahydropalmatine and Bamatin were measured in the alcohol elution to calculate elution rate and purity.

Figure 11:
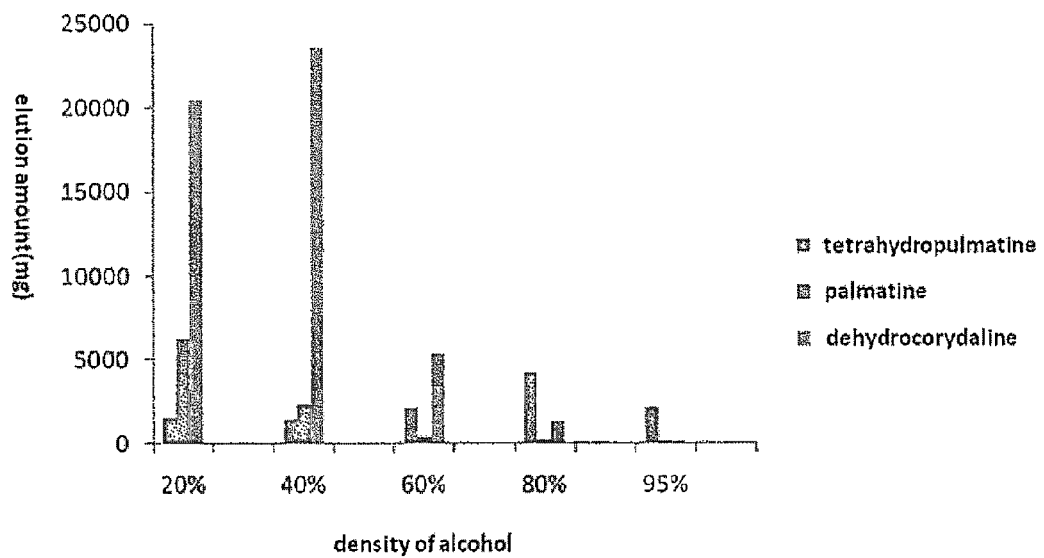
FIG. 11 Observation of the ethanol elution concentration of D101 resin-Comparison of the elution volume.

It can be seen from the figure that the water-soluble alkaloids and the fat-soluble alkaloid was eluted in different concentration of alcohol after ethanol gradient elution, the water-soluble alkaloids can be eluted with 40% alcohol, the fat-soluble alkaloid was eluted with 95% alcohol, and both of them can be eluted directly with 95% ethanol, therefore, the 95% ethanol was chosen as the alcohol elution 9.2 Investigation of the Concentration of Ethanol Elution by D101 Resin 10 mL of D101 macroporous resin processed was packed in the same type of chromatography columns, the sample solution 70 mL was drew precisely, adsorbed dynamically with the flow rate of 0.4 mL/min, washed four column volumes, the flow rate was 0.4 mL/min, and then, washed successively with 20%, 40%, 60%, 80%, and 95% ethanol three column volumes of elution, the flow rate was 0.4 mL/min, the content of three components were measured in each alcohol elution, the results show in FIG. 11:

It can be seen from the figure that the water-soluble alkaloids can be eluted at low concentration of alcohol, and as tertiary amine type water insoluble alkaloid, tetrahydropalmatine elution rate reached the maximum in 80% ethanol, Considered as a whole, it was decided to choose 80% ethanol as eluent.

10 Investigation of the Ethanol Elution Volume

10.1 Investigation of the Ethanol Elution Volume in HPD300 Resin 10 mL of the processed macroporous resin was packed in the same type of chromatography columns, the sample solution 60 mL was drew precisely, adsorpted dynamicly with the flow rate of 0.6 mL/min, washed three column volumes, and then, eluted with 95% ethanol 15 BV, calculated the cumulative elute rate of dehydrocorydaline, Bamatin, and tetrahydropalmatine.

TABLE 9

Investigation of the ethanol elution volume in HPD300 resin (n = 2)

| Multiples of elution | Dehydrocorydaline % | Bamatin % | Tetrahydropalmatine % |
|---|---|---|---|
| 1 BV | 39.05 | 55.53 | 16.59 |
| 2 BV | 64.67 | 87.72 | 52.08 |
| 3 BV | 72.16 | 92.72 | 70.51 |
| 4 BV | 73.15 | 94.07 | 80.75 |
| 5 BV | 73.67 | 94.78 | 87.4 |
| 6 BV | 73.97 | 95.19 | 91.01 |
| 7 BV | 74.26 | 95.55 | 93.65 |
| 8 BV | 74.61 | 95.96 | 95.42 |
| 9 BV | 74.81 | 96.22 | 96.58 |
| 10 BV | 74.95 | 96.42 | 97.46 |
| 11 BV | 75.01 | 96.6 | 98.04 |
| 12 BV | 75.06 | 96.64 | 98.45 |
| 13 BV | 75.09 | 96.7 | 98.75 |
| 14 BV | 75.12 | 96.72 | 98.99 |
| 15 BV | 75.16 | 96.72 | 99.27 |

Figure 12:
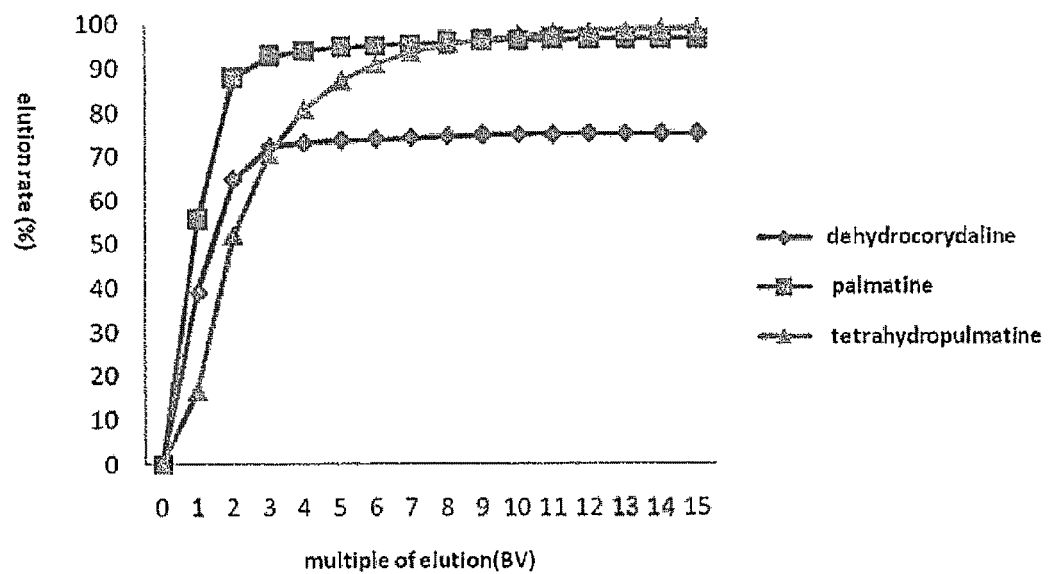
FIG. 12 Observation of the ethanol elution volume of HPD300 resin (n=2)

It can be seen from the experimental results in FIG. 12 that the elution rate of Bamatin in the 6 BV can reach more than 95% using 95% ethanol elution, tetrahydropalmatine in 8 BV can reach above 95%, dehydrocorydaline elution rate is 78% at all.

10.2 Investigation of the Ethanol Elution Volume in D101 Resin 10 mL of the processed macroporous resin was packed in the same type of chromatography columns, the sample solution 70 mL was drew precisely, adsorpted dynamicly with the flow rate of 0.4 mL/min, washed four column volumes, and then, eluted with 80% ethanol 10 BV, each of the 10 mL eluent is collected once, the contents and the paste volume of three kinds of components in the volume of each alcohol elution were measured. The results show in table 10 and FIG. 13:

TABLE 10

Investigation of the ethanol elution volume in D101 resin (n = 2)

| Multiples of elution | Cumulative elution rate/% | | |
|---|---|---|---|
| | Bamatin | Dehydrocorydaline | Tetrahydropalmatine |
| 1 | 67.38 | 59.38 | 35.84 |
| 2 | 96.99 | 92.445 | 67.27 |
| 3 | 98.37 | 94.145 | 78.175 |
| 4 | 98.785 | 94.66 | 85.695 |
| 5 | 98.975 | 94.885 | 91.55 |
| 6 | 99.11 | 95.02 | 95.42 |
| 7 | 99.195 | 95.105 | 98.18 |
| 8 | 99.26 | 95.155 | 100.115 |
| 9 | 99.26% | 95.18 | 101.325 |
| 10 | 99.27 | 95.205 | 102.05 |

Figure 13:
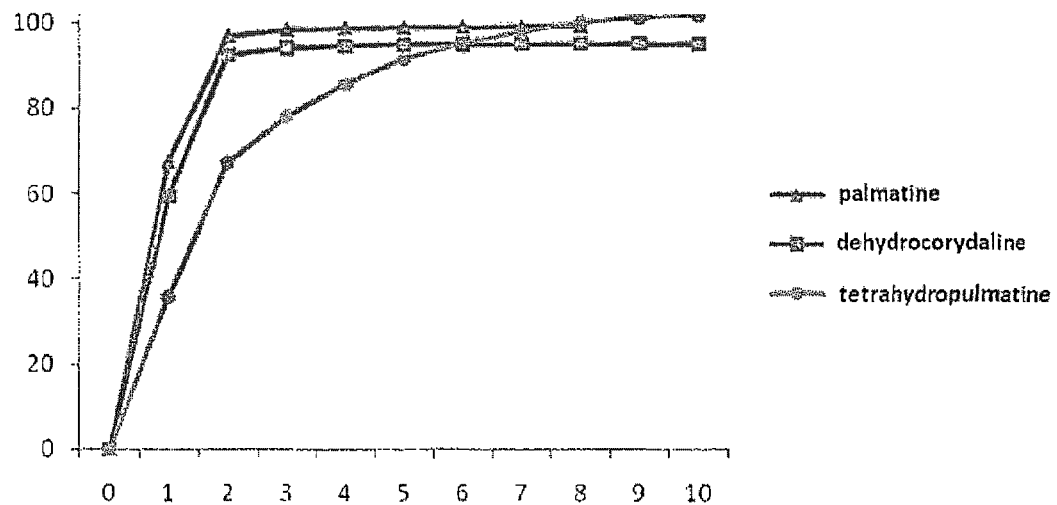
FIG. 13 Observation of the ethanol elution volume of D101 resin (n=2)

It can be seen from the results in FIG. 13 that the elution rate of three components can reach more than 95% when the elution volume is 8 times the column volume, therefore, it is decided to choose the elution volume is 8 times the column volume.

11 Improving the Technology of HPD300 Resin

When using of HPD300 resin, the elution rate of dehydrocorydaline is low, therefore, by improving the loading and elution conditions, the elution rate of dehydrocorydaline can be optimized.

11.1 Elution by Using Alkaline Ethanol 10 mL of the processed macroporous resin was packed in the same type of chromatography columns, 60 mL of the sample solution was drew precisely, adsorpted dynamicly with the flow rate of 0.6 mL/min, washed three column volumes.

And then, 95% ethanol 120 mL, added NaOH to adjust the pH value to 8.5, elution flow rate was 0.6 mL/min, elution volume 12 BV, collected the eluent, determinated of the cumulative elution rate of three components.

TABLE 11

Investigation of the alkaline ethanol elution volume in HPD300 resin (n = 2)

| Multiples of elution | Dehydrocorydaline | Bamatin | Tetrahydropalmatine |
|---|---|---|---|
| 1BV | 46.01 | 52.66 | 6.81 |
| 2BV | 68.44 | 70.27 | 42.34 |
| 3BV | 72.83 | 74.27 | 68.25 |
| 4BV | 75.26 | 76.74 | 81.25 |
| 5BV | 76.92 | 78.64 | 90.21 |
| 6BV | 78.12 | 80.18 | 95.31 |
| 7BV | 78.98 | 81.49 | 98.48 |
| 8BV | 79.63 | 82.62 | 100.58 |
| 9BV | 80.12 | 83.54 | 102.01 |
| 10BV | 80.52 | 84.31 | 103 |
| 11BV | 80.84 | 84.97 | 103.74 |
| 12BV | 81.11 | 85.54 | 104.28 |

Figure 14:
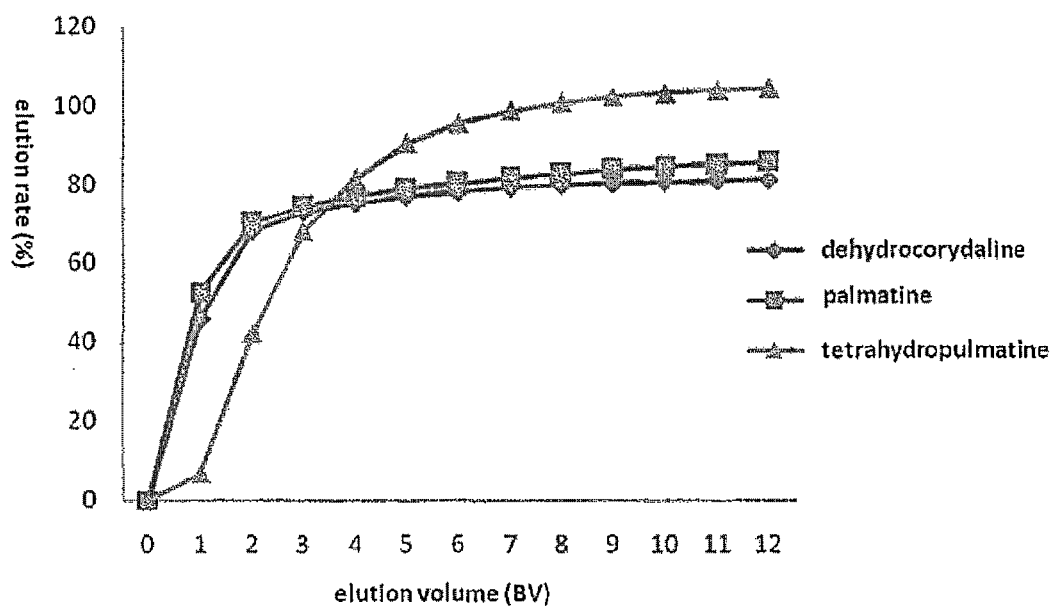
FIG. 14 Observation of the alkaline ethanol elution volume of HPD300 resin (n=2)

From the experimental results in Table 11 and FIG. 14, it due to the increasing of dehydrocorydaline elution rate that the ethanol was alkalified, but the effect is not obvious, the elution rate is only around 80%, while Bamatin elution rate declined.

11.2 The Macroporous Resin Column was Activated by Sodium Hydroxide Solution 10 mL of the processed macroporous resin was packed in the same type of chromatography columns, the sample solution 60 mL was drew precisely, adsorpted dynamicly with the flow rate of 0.6 mL/min, washed three column volumes.

And then, 0.1 mol/L NaOH solution 120 mL, eluted volume 3 BV, the flow rate was 0.6 mL/min, taked place for 1 h, received the eluent, determinated of the cumulative elution rate of three components 95% ethanol eluted volume 10 BV, calculated the cumulative elution rate of three components.

TABLE 12

Investigation of the alkaline ethanol elution volume in HPD300 resin activated by alkaline solution(n = 2)
Average elution rate %

| | Dehydrocorydaline | Bamatin | Tetrahydropalmatine |
|---|---|---|---|
| Washed by alkaline solution1 | 0.03 | 0 | 0 |
| Washed by alkaline solution2 | 0.1 | 0 | 0 |

TABLE 12-continued

Investigation of the alkaline ethanol elution volume in
HPD300 resin activated by alkaline solution(n = 2)
Average elution rate %

|  | Dehydrocorydaline | Bamatin | Tetrahydropalmatine |
|---|---|---|---|
| Washed by alkaline solution3 | 0.18 | 0 | 0 |
| 1 | 13.25 | 7.385 | 9.305 |
| 2 | 30.025 | 24.46 | 44.725 |
| 3 | 41.74 | 38.325 | 66.78 |
| 4 | 48.035 | 46.69 | 80.025 |
| 5 | 52.315 | 53.11 | 87.445 |
| 6 | 55.11 | 57.76 | 99.31 |
| 7 | 57.085 | 61.55 | 101.9 |
| 8 | 58.385 | 64.3 | 103.485 |
| 9 | 59.425 | 66.665 | 104.575 |
| 10 | 60.08 | 68.475 | 105.33 |

Figure 15:
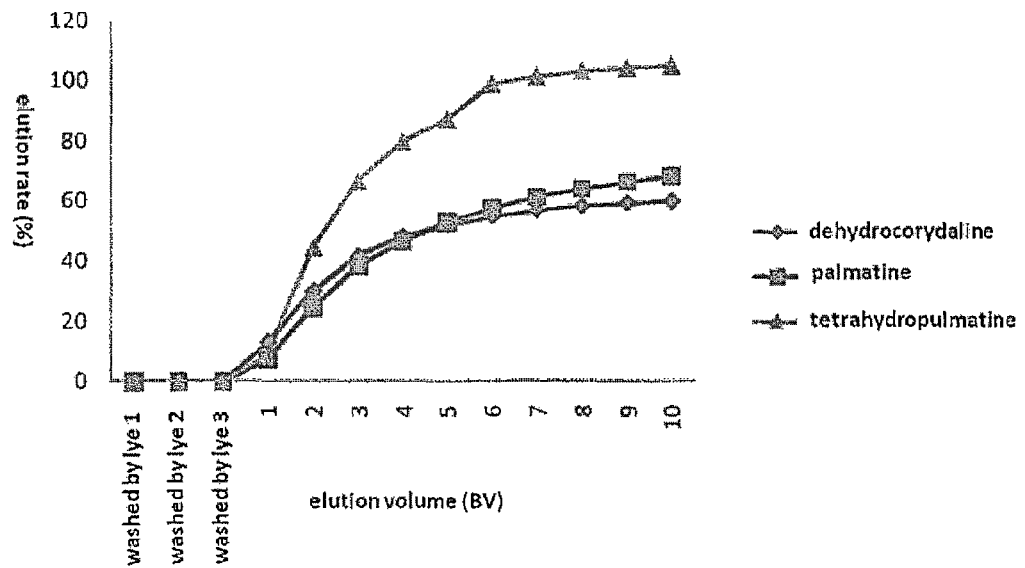
FIG. 15 The cumulative elution rate of each component after activation using alkaline of HPD300 resin.

From the results in Table 10 and FIG. 15, the elution rate of quaternary amine base components is decreased because of the alkaline activation, the cumulative elution of dehydrocorydaline is 60%, the cumulative elution of Bamatin is about 68%, tetrahydropalmatine can be completely eluted at 10 BV.

Because of the elution rate of dehydrocorydaline is not high, it is considered that the type of resin was selected inappropriately. Considered as a whole, it is decided to choose 80% ethanol as eluent.

12 The Washed Flow Rate and Volume of D101 Resin 10 mL of D101 macroporous resin processed was packed in two chromatography columns (12 mmI.D.), 70 mL of the sample solution was drew precisely, loaded dynamicly with the flow rate of 0.4 mL/min, and then, washed with distilled water till Molish reaction was negative. Molish reaction: Take 1 mL cleaning solution, add two drops of Molish reagent, shake. Inclined tube, along the wall of the tube carefully add 1 mL of concentrated sulfuric acid, do not shake, after careful vertical, carefully observed the color change of the surface at the junction of two layers. The results found washed up to 4 times the column volume of water, cleaning liquid was near colorless, Molish reaction was negative, no leakage of water Determination of alkaloids in the fluid alkaloid reagents, the water volume was determined to 4 BV.

13 Investigation of the Ethanol Elution Speed 10 mL of the processed macroporous resin was packed in the same type of chromatography columns, 70 mL of the sample solution was drew precisely, adsorbed dynamicly with the flow rate of 0.4 mL/min, washed four column volumes, the flow rate was 0.4 mL/min, and then, eluted successively with 80% ethanol 10 times column volumes, the flow rate was 0.6 mL/min and 0.8 mL/min, the content of three components were measured in each alcohol elution. Calculate the elution rate and the extract rate. The results are listed in the following table

TABLE 13

Investigation of the ethanol elution speed of D101 resin (n = 2)

| The ethanol elution speed (mL/min) | The elution rate | | | The extract rate | Purity | | |
|---|---|---|---|---|---|---|---|
| | Dehydro-corydaline | Bamatin | Tetrahydro-palmatine | | Dehydro-corydaline | Bamatin | Tetrahydro-palmatine |
| 0.6 | 92.27 | 86.94 | 101.16 | 1.41% | 14.81 | 2.77 | 4.17 |
| 0.8 | 92.13 | 86.50 | 97.90 | 1.36% | 15.39 | 2.87 | 3.69 |

Comparison of the elution rate of three components, the group of the flow rate of 0.6 mL/min is higher, and the extract rate is slightly larger, the flow rate of 0.6 mL/min is selected in line with the principle of eluted completely.

14 Investigation of the Diameter Height Ratio

The processed macroporous resin 6.8 mL, 10 mL, and 12.2 mL were packed in the same type of chromatography columns respectively, the diameter height ratio respectively were 1:5, 1:7, and 1:9, respectively the sample solution 47.6 mL, 70 mL, and 85.4 mL were drew precisely, adsorbed dynamicly with the flow rate of 0.4 mL/min, washed three column volumes (0.4 mL/min), eluted with 80% ethanol 8 times column volumes (0.6 mL/min), the content and the extract rate of Dehydrocorydaline, Bamatin, and Tetrahydropalmatine were measured in each alcohol elution, and calculate the elution rate and the purity.

TABLE 14

Investigation of diameter height ratio of D101 resin (n = 2)

| Diameter height ratio | The elution rate | | | Purity | | |
|---|---|---|---|---|---|---|
| | Dehydro-corydaline | Bamatin | Tetrahydro-palmatine | Dehydro-corydaline | Bamatin | Tetrahydro-palmatine |
| 1:5 | 85.71 | 96.32 | 81.09 | 11.2 | 2.32 | 3.24 |
| 1:7 | 91.18 | 101.55 | 90.24 | 11.49 | 2.36 | 3.48 |
| 1:9 | 95.69 | 99.64 | 86.21 | 11.47 | 2.2 | 3.15 |

It can be seen from the results that the diameter height ratio is less affected on the results, the diameter height ratio of 1:7 is selected considering the needs of actual production.

15 Laboratory Test

According to the enrichment of purification process for preparation of the macroporous adsorption resin above, three batches of sample is prepared, and determinated the content of total alkaloid.

TABLE 15

Verification of macroporous resin procession

| | Weight/mg | Concentration | Absorbance | Content/% |
|---|---|---|---|---|
| Control | 5.7 | 0.228 | 1.0446 | |
| Sample1 | 6.3 | 0.126 | 0.4026 | 69.74 |
| Sample2 | 5.6 | 0.112 | 0.3464 | 67.51 |
| Sample3 | 5.64 | 0.1128 | 0.3456 | 66.87 |
| Average | | | | 68.04 |

Figure 16:
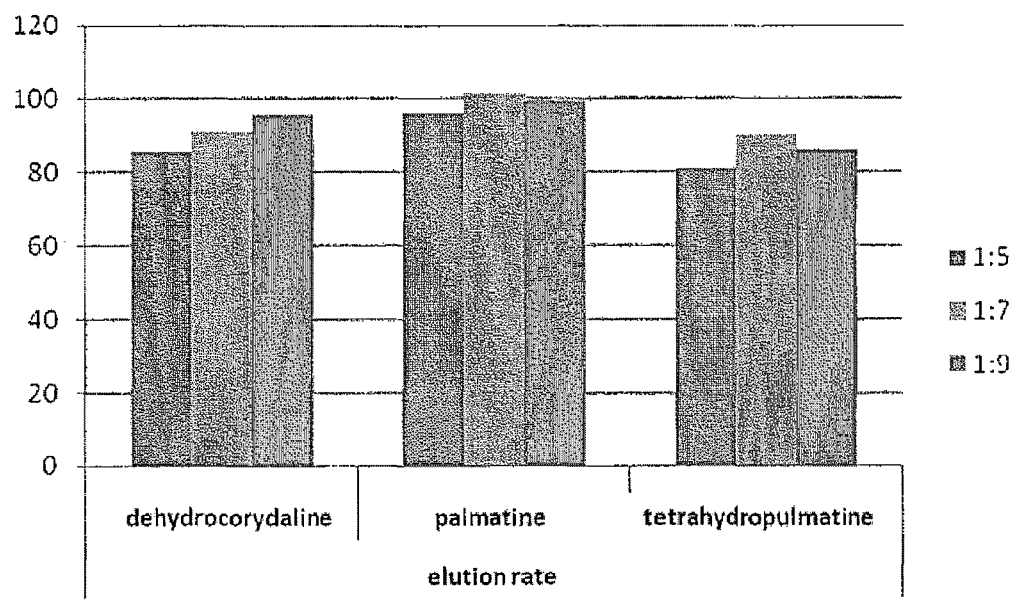
FIG. 16 Observation of the ratio of diameter to height and elution rate of D101 resin.
Figure 17:
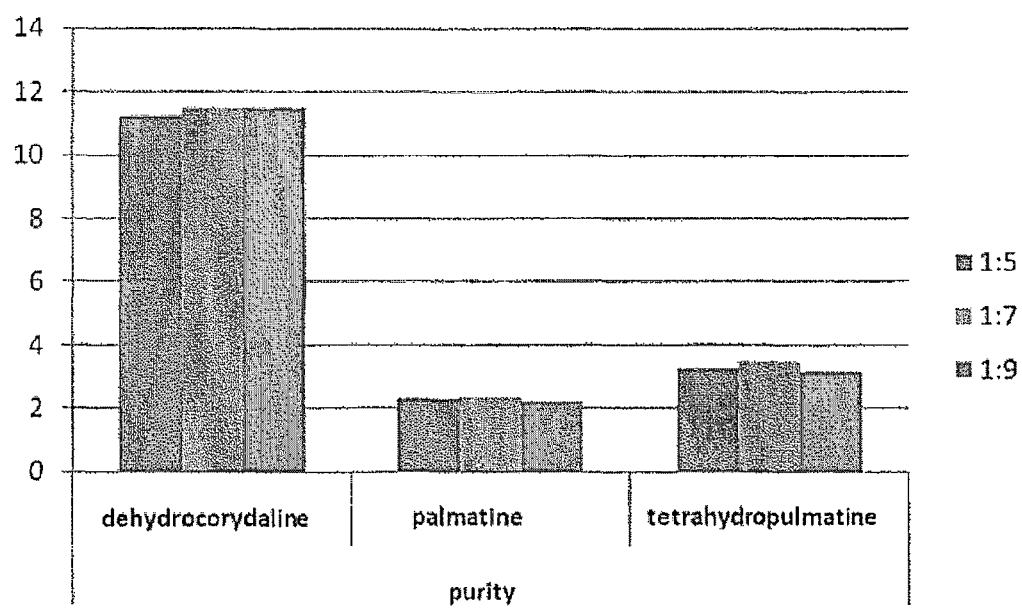
FIG. 17 Observation of the ratio of diameter to height and purity of D101 resin.

The experimental results of FIG. 16 and FIG. 17 show that the purification process is stable and feasible.

Macroporous resin technology Summary: D101 macroporous resin, the sample concentration was 0.3 g/mL, adjust the sample solution pH 1.5 precipitate dissolved, diameter to height ratio of 1:7, the sample volume of 2.1 g crude drug/mL resin, washing impurity removal volume of 4 BV, the flow rate was 0.4 mL/min, eluent ethanol concentration of 80%, elution flow rate of 0.6 mL/min, elution volume was 8 BV.

EXPERIMENTAL EXAMPLE 4

1 Materials and Methods 1.1 Materials
1.1.1 Animals

Healthy Wistar male rats, weight 200 to 220 g, were supplied by Beijing HFK Bioscience Co., Ltd
Serial no.: SCXK Beijing 2009-0007.
1.1.2 Instruments and Equipment Scanner Phantom V7 was supplied by Sino Krystal Technology. DT-2000 electronic scale was made by Two Brothers Co. Ltd. MPIDS-500 multimedia pathology color image system was manufactured by Beijing Kong Hai Science and Technology Development Co Ltd.
1.1.3 Medicines and Reagents The extract of Rhizoma Corydalis, yellowish powder, was obtained by conducting the experiment in example 3, Batch no. 1: 201107. One gram of the extract was equivalent to 62.762 grams of crude medicinal; Batch no. 2: 201107. One gram of the extract was equivalent to 65.50218 grams of crude medicinal.

Metoprolol, 25 mg/tablet, was supplied by AstraZeneca Pharmaceutical Co. Ltd. Batch no.: 1105031.

Shengsong Yangxin capsule, 0.4 g/capsule, was prepared by Hebei Yiling Pharmaceutical Co. Ltd., Batch no. 1104007.

Nitrotetrazolium blue chloride (N-BT) was supplied by Amresco, Batch no.: 2541C012.

Chloral hydrate was supplied by Sinopharm Chemcial Reagent Co. Ltd., Batch no.: 20110210.
1.2 Methods
1.2.1 Animal Models Establishment The rats were fixed on their back on board and chloral hydrate (10 mg/kg) intraperitoneally administered. Between the rib 4 and 5 on the left side, an open was cut into pleural cavity and the pericardium was torn open, then the heart was extruded by light pressure to the thorax. Two mm beneath left auricle, a ligation was done on left anterior descending artery with surgical suture (USP 0) and the heart was put back to the thorax. The cut open was closed and stitched. Penicillin (up to 80,000 unit) was used for the incision to protect again infection.
1.2.2 Grouping Sixty-six rats models were randomly assigned to 6 groups, 11 for each. They were the model group, the Metoprolol group, the Shengsong Yangxin capsule group, the large-dose extract group, the moderate-dose extract group and the small-dose extract group.
1.2.3 Medicines Doses and Preparation 1) The Metoprolol group. Due to the administration of β receptor inhibitor after myocardial infarction (MI), Metoprolol was administered initially at small dose of 12.5 mg, bid, that is, the dosage was 25×0.018×5=2.25 mg/kg. Metoprolol 67.5 mg was accurately weighed and evenly dissolved with 300 ml normal saline (0.9%).

2) The Shengsong Yangxin capsule group. The capsule was administered, 4 capsules, tid, 0.4 g/capsule. The dosage for a rat was 4.8×0.018×5=0.432 g/kg. The medicinal, filled Shengsong Yangxin capsule, of 12.96 g were accurately weighed and evenly dissolved with 300 ml normal saline (0.9%).

3) The groups treated with the extract. According to the Pharmacopeia, the biggest dose of Rhizoma Corydalis was 9 g. Accordingly, 0.81 g/kg (9×0.018×5) was the dose for the small-dose group; 1.62/kg for the moderate-dose group; 3.24 g/kg for the large-dose group. According to the dose of 10 ml/kg, 0.324 g/ml was the concentration for the large-dose extract group. Prepared was 400 ml, that is, the crude medicinal was 129.6 g (400×0.324). Its extractum of 4.78 g was equivalent to 300 g crude medicinal and 129.6 g crude medicinal was equal to 2.06496 g extractum. The extractum of 2.06496 g was accurately weighed and dissolved with 400 ml normal saline prepared for the large-dose extract group. The solution of 110 ml was taken from the solution for the large-dose extract group and diluted evenly with 110 ml normal saline, then the 220 ml solution was used for moderate-dose extract group. The solution of 60 ml was taken from the large-dose group and diluted evenly with 180 ml normal saline, then the 240 ml solution was used for small-dose extract group.

4) The model group. The same volume of normal saline was given according to the dose of 1 ml/100 g.
1.2.4 Treatments Administration Starting from the next day after model establishment, treatments were administered intragastrically for 7 days.
1.2.5 Assessment of the Areas of Myocardial Infarction (MI) of the Rats The hearts of the rats were harvested 2 hours after the last treatments were administered and the residues of blood in the heart chambers were washed with normal saline. After the residual water was absorbed away with filter paper, the hearts were weighed. Starting from the position beneath the ligation and, the hearts were all cut parallel to the coronary sulcus into 5 slices with the same thickness. The slices were all weighed and stained for 2 minutes with 0.2% N-BT at room temperature. Both sides of all slices were scanned and the images obtained were blindly re-numbered. Armed with the MPIDS-500, two technicians measured the MI areas on both sides of the slices. Using the average values of the two technicians, the total areas of ventricular chambers, total MI areas and ratio of MI areas to total areas of ventricular chambers were obtained.

1.4 Data Analysis

Data were processed with SPSS 16.0. One-way ANOVA was performed and P<0.05 was the significant level.

Figure 19:
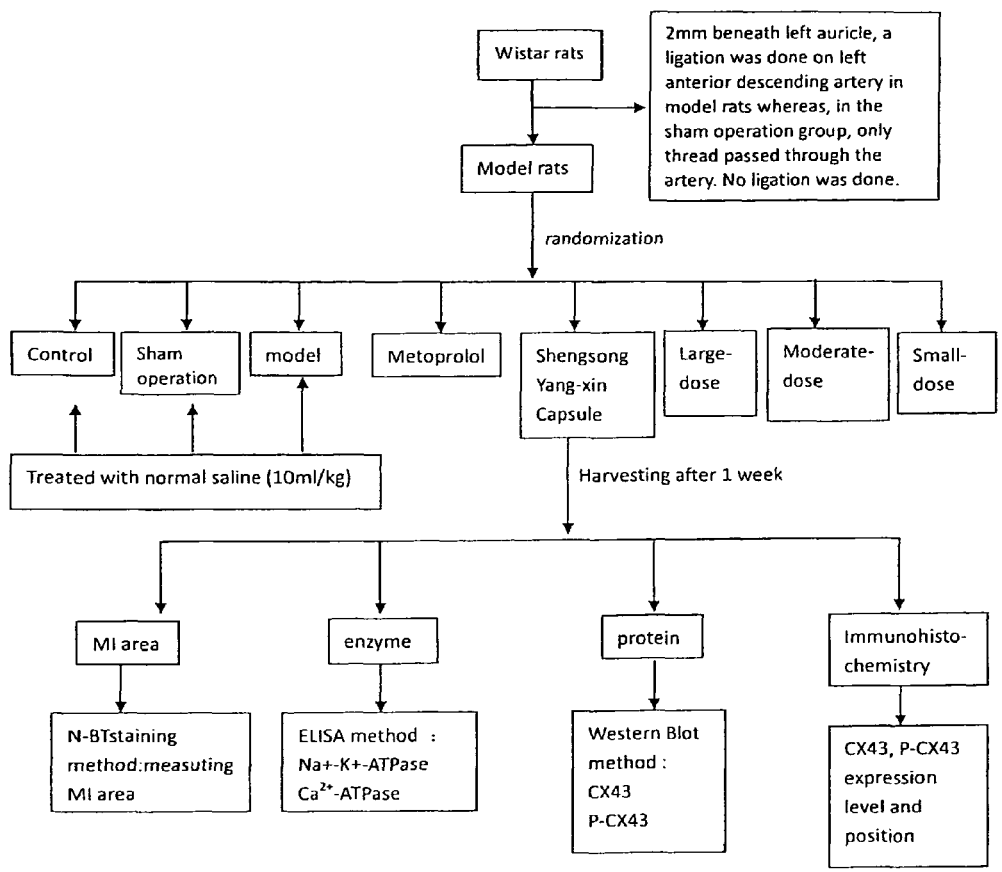
FIG. 19 Procedure flowchart.

2. Procedure Flowchart (See FIG. 19)

3. Results

Before intragastrical administration, dead were 2 rats in model group, 1 in Metoprolol group, 2 in Shengsong Yangxin capsule group, 1 in the moderate-dose extract group and 1 in the small-dose extract group.

TABLE 1

MI areas of all groups ($\bar{x} \pm SD$)

| Group | dose | n | total area of ventricular chamber | MI area | MI area/total area of ventricular chamber (%) |
|---|---|---|---|---|---|
| Model | — | 9 | 33.5817 ± 2.29664 | 7.8122 ± 1.21987 | 23.2192 ± 2.98284 |
| Metoprolol | 2.25 mg/kg | 10 | 32.3830 ± 6.86562 | 6.1945 ± 1.79495** | 19.0847 ± 2.81914** |
| Shengsong | 0.432 g/kg | 9 | 33.5633 ± 2.55042 | 6.2194 ± 0.86266** | 18.5298 ± 2.15456** |
| Large-dose | 3.24 g/kg | 11 | 35.6805 ± 5.57962 | 7.2540 ± 1.37520Δ▲ | 20.4177 ± 3.06969* |
| Moderate dose | 1.62 g/kg | 10 | 32.4036 ± 2.81088 | 5.9814 ± 1.22618** | 18.4242 ± 3.23239** |
| Small-dose | 0.81 g/kg | 11 | 34.8118 ± 3.26870 | 6.1482 ± 1.08577** | 17.6981 ± 2.92249**Δ |
| F | | | 1.003 | 3.788 | 5.916 |
| P-value | | | 0.425 | 0.005 | 0.0001 |

Compared with the model group,
*p < 0.05,
**p < 0.01;
compared with the Metoprolol group,
Δp < 0.05,
ΔΔp < 0.01;
compared with the Shengsong Yangxi capsule group,
▲P < 0.05,
▲▲P < 0.01.

The ventricular areas of the hearts in all groups were compared. They were not significantly different from one another (p=0.425). For MI areas, compared with model group, MI areas in the groups treated with Metoprolol, Shengsong Yangxin capsule, moderate dose and small dose of the extract were significantly reduced (p<0.05) except that in the large-dose extract group; compared with the Metoprolol group, MI area in large-dose extract group was marginally significantly different (p<0.05) and for the rest of treatment groups, no significant difference was found; compared with the Shengsong Yangxin capsule group, only the MI area in large-dose extract group was marginally significantly different and for the rest of treatment groups, no significant difference was found. For the ratio of MI area to total area of ventricular chamber, compared with model group, the ratios in all treatment groups were significantly decreased (p<0.05); compared with Metoprolol group, the ratio of small-dose extract group was smallest whereas no significant difference was found in the rest of treatment groups; compared with the Shengsong Yangxin capsule group, no significant difference was found in all treatment groups. The study suggested that small dose and moderate dose extract could significantly reduce MI areas and improve the ischemia so as to reduce the incidence of ischemic arrhythmia. Its effect was similar to that of Metoprolol or the Shengsong Yangxi capsule, and even better.

4 Discussion

In the models, the ligation of left anterior descending artery resulted in myocardial ischemia and arrhythmia was induced. This is similar to the arrhythmia induced by acute MI. The frequency of the onset of arrhythmia is positively associated with the degree of myocardial ischemia. When myocardial ischemia is severe, significant changes in the metabolism of cardiac muscle, cell structure and ionic channel are changed greatly and the oxidative metabolism is reduced in mitochondria. Myocardial phosphatase are activated and phosphonolipide is decomposed. Free fatty acid in blood increases. Oxygen-derived free radicals accumulate in ischemic area, which leads to the ischemic damage to cardiac muscles. Regional cardiac muscles response to catecholamine is poor. The difference of transient outward potassium currents between outer membrane, middle membrane and inner membrane increase, which induces J wave and ST segment elevation. The transmural dispersion of repolarization increases. This creates unbalanced myocardial repolarization, then leads to reentrant rhythm and induces arrhythmia. By coronary perfusion, a canine model of ventricular wedge was created. Using floating glass microelectrode and ECG for simultaneous recording, the status of acute myocardial ischemia was scrutinized for 20 minutes. The rate of ventricular premature contraction (VPC) was 63.6% and the R on T VPC and ventricular tachycardia may occur. Moreover, during the early stage of acute myocardial ischemia, Ito of inner, middle, and outer layers of myocardium increased and the action potential was shorten. Thus the transmural dispersion of repolarization increased and phase 2 reentry ensued. It is the primary mechanism underlying the ventricular arrhythmias. Besides, due to the ischemia, ligandins between cells lost coupling and their number decreased. This resulted in slow conduction velocity in heart and spontaneous or secondary VPC induced ventricular fibrillation.

The outcomes of the study revealed that the extract of Rhizoma Corydalis could significantly reduce MI area and the ratio of MI area to total of ventricular area, correst myocardial ischemia, and reduce the incidence of arrhythmia.

EXPERIMENTAL EXAMPLE 5

1 Materials and Methods 1.1 Materials
1.1.1 Animals

Healthy Wistar male rats, weight 200 to 220 g, were supplied by Beijing HFK Bioscience Co., Ltd
Serial no.: SCXK Beijing 2009-0007.

1.1.2 Instruments and Equipment

DT-2000 electronic scale was made by Two Brothers Co. Ltd.

Enzyme-labelled meter 352 was manufactured by Labsystems Multiskan, Finland.

Microplate washer AC8 was made by Thermo Labsystems, Finland.

High speed micro-centrifuge TG16W was manufactured in China.

Water jacket incubator GNP-9080 was made in China.

High speed dispersers FSH-2 was manufactured by Jinnan Instruments Manufacturing Co. Ltd.

1.1.3 Medicines and Reagents

The extract of Rhizoma Corydalis, yellowish powder, was obtained by conducting the experiment in example 3, Batch no. 1: 201107. One gram of the extract was equivalent to 62.762 grams of crude medicinal; Batch no. 2: 201107. One gram of the extract was equivalent to 65.50218 grams of crude medicinal.

Metoprolol, 25 mg/tablet, was supplied by AstraZeneca Pharmaceutical Co. Ltd. Batch no.: 1105031.

Shengsong Yangxin capsule, 0.4 g/capsule, was prepared by Hebei Yiling Pharmaceutical Co. Ltd. Batch no. 1104007.

Chloral hydrate was supplied by Sinopharm Chemcial Reagent Co. Ltd. Batch no.: 20110210. $Na^+k^+$ ATPase assay kit and $Ca^{2+}$-ATPase assay kit were supplied by IBL, Germany. Batch no. 201108.

1.2 Methods 1.2.1 Animal Models Establishment

The rats were fixed on their back on board and chloral hydrate (10 mg/kg) intraperitoneally administered. Between the rib 4 and 5 on the left side, an open was cut into pleural cavity and the pericardium was torn open, then the heart was extruded by light pressure to the thorax. Two mm beneath the left auricle, a ligation was done on left anterior descending artery with surgical suture (USP 0) and the heart was put back to the thorax. The cut open was closed and stitched. Penicillin (up to 80,000 unit) was used for the incision to protect again infection.

1.2.2 Grouping

Forty-two rats models were randomly assigned to 6 groups, 7 for each. They were the model group, the Metoprolol group, the Shengsong Yangxin capsule group, the large-dose extract group, the moderate-dose extract group, the small-dose extract group. Added were a control group of 6 rats and sham operation group of 6 rats. Totally there were 8 groups.

1.2.3 Medicines Doses and Preparation. See Section 1.2.3 in the Experiment Example 1.

1.2.4 Treatment Administration

Starting from the next day after model establishment, the medicines were all administered intragastrically to the relevant groups accordingly, while the model group and sham operation group were given normal saline. The treatment course lasted for 7 days.

1.3 Assessment of MI Areas

The hearts of the rats were harvested by cutting off the MI areas below the ligation points and the residues of blood in the heart chambers were washed with normal saline, then PBS, pH 7.4, was added and they were stored instantly with liquid nitrogen.

$Na^+$—$K^+$-ATPase and $Ca^{2+}$-ATPase tests were conducted following the instructions on the kits. The procedure is as follows:

1) Thawing the frozen heart and then maintaining the temperature at 2-8° C.; weighing the cardiac muscles and adding proper amount of PBS, then thoroughly homogenizing them to produce 20% cardiac tissue homogenate; performing centrifugation at 2000 rpm for 20 minutes, then collecting the supernatant.

2) Sample dilution and sample injection

Following the instruction on the kit for sample dilution to prepare 5 gradients. The concentration were 1200 ug/L, 800 ug/L, 400 ug/L, 200 ug/L, 100 ug/L respectively and adding 50 ul to each well of all gradients.

3) Sample Injection

Control wells and wells to be tested were set up. The 40 ul sample-diluted solution was added to the to-be-tested-sample well on the plate of the kit, then 10 μl of the to-be-tested sample was added to the bottom of the plate without touching the side wall of the well, then they were mixed with gentle shake.

4) Incubation

The plate was sealed with parafilm and placed in incubator at 37° C. for 30 minutes.

5) Washed with the Prepared Liquid

The 30-time concentrated washing solution was diluted 1:30 times with distilled water; removing the parafilm with care and discarding the liquid and performing centrifugation; fully adding washing solution to each well; letting stand for 30 seconds, then discarding the washing solution; repeating the procedure for 5 times, then letting them dried.

6) Adding the Enzymes

Reagent of 50 μl was added to each well except for the control well.

7) Incubation

The plate was sealed with parafilm and incubated at 37° C. for 30 minutes.

8) Washing

Removing the film with care and discarding the liquid and centrifuging the plate, the fully adding each well with washing solution, letting stand for 30 seconds, the discarding the liquid; repeating the procedure for 5 times and letting the plate dried.

9) Color Development

Adding color development reagent A 50 μl to each well, and then adding reagent B 50 μl, and gently shaking the plate for even mixture, and letting the color develop for 15 minutes at 37° C. away from light.

10) Adding 500 of the termination solution to each well to terminate the reaction.

11) Measurement

Measuring the optical density (OD) of each well at 450 nm by setting the control as null reference. This was done 15 minutes after adding terminating solution.

12) OD calculation

X axis was the concentration of standard sample and y axis was OD's value and the standard curve was drawn on the coordinate plane; the tested sample's concentration could be obtained in two ways: by matching the OD value of a sample to the standard curve, the corresponding concentration on the curve could be read. The tested sample's concentration was obtained by multiplying the concentration by the diluted times; the other way is using the linear regression model of the standard curve to estimate the concentration. The model could be generated with OD values and concentration of the standard sample. Then the tested sample's concentration was obtained by multiplying the estimated concentration by the diluted times.

1.4 Data Analysis

Data were processed with SPSS 16.0. The values were described as ($7\pm SD$). One-way ANOVA was conducted. A linear regression line was fit to data of OD values and concentrations. $P<0.05$ was the significant level.

2 Procedure Flowchart. See FIG. 19.

3 Results 3.1 The Outcomes of $Na^+$—$K^+$-ATPase Test
3.1.1 The Linear Regression of the Standard Sample

TABLE 2

OD values and concentrations of standard sample

|  | S1 | S2 | S3 | S4 | S5 |
|---|---|---|---|---|---|
| OD | 0.22 | 0.45 | 0.822 | 1.345 | 1.872 |
| Concentration (U/ml) | 0.75 | 1.5 | 3 | 6 | 9 |

The regression line fitting the data was $y = -0.725 + 5.071x$, $r = 0.996$.

3.1.2 Concentrations of $Na^+$-$k^+$-ATPase

TABLE 3

Concentrations of $Na^+$-$k^+$-ATPase ($\bar{x} \pm SD$)

| Group | n | concentration (U/ml) | F (welch) | P-value |
|---|---|---|---|---|
| Control | 6 | 10.7267 ± 0.20435** |  |  |
| Sham operation | 5 | 9.4765 ± 0.15045** |  |  |
| Model | 6 | 5.2274 ± 0.52888** |  |  |
| Metoprolol | 7 | 10.1177 ± 0.16701**ΔΔ |  |  |
| Shengsong Yangxin | 7 | 9.7218 ± 0.19141**ΔΔ▲▲ | 299.182 | 0.0001 |
| Large-dose | 7 | 7.0156 ± 0.27422**ΔΔ▲▲ |  |  |
| Moderate-does | 7 | 9.3426 ± 0.16323**ΔΔ▲▲ |  |  |
| Small-dose | 7 | 8.1058 ± 0.25298**ΔΔ▲▲ |  |  |

Compared with the control group,
*p < 0.05,
**p < 0.01;
compared with the model group,
ΔP < 0.05,
ΔΔP < 0.01;
Compared with the Metoprolol group,
▲P < 0.05,
▲▲P < 0.01.

The results revealed that, compared with the control group, the $Ca^{2+}$-ATPase concentrations of the rest of groups, especially the model group, significantly decreased (p<0.01), that, compared with the model, the concentrations of all treatment groups all increased significantly (p<0.01), and that, compared with the Metoprolol group, the concentrations in the Shengsong Yangxin capsule group and the three groups treated with the extract were a bit low.

3.2 The Concentrations of $Ca^{2+}$-ATPase
3.2.1 The Linear Regression of the Standard Sample

TABLE 4

OD values and concentrations of standard sample

|  | S1 | S2 | S3 | S4 | S5 |
|---|---|---|---|---|---|
| OD value | 0.194 | 0.426 | 0.766 | 1.24 | 1.871 |
| concentration (U/ml) | 1.25 | 2.5 | 5 | 10 | 15 |

The regression line fitting the OD values and concentrations was $Y = -0.871 + 8.473X$, $r = 0.997$.

3.2.2 The Concentrations of $Ca^{2+}$-ATPase

TABLE 5

The concentrations of $Ca^{2+}$-ATPase ($\bar{x} \pm SD$)

| Group | n | concentration (U/ml) | F | P-value |
|---|---|---|---|---|
| Control | 6 | 19.2932 ± 0.44689** |  |  |
| Sham operation | 5 | 16.3923 ± 0.21388** |  |  |
| Model | 6 | 8.7333 ± 0.26976** |  |  |
| Metoprolol | 7 | 17.5339 ± 0.24390**ΔΔ |  |  |
| Shengsong Yangxin | 7 | 13.8123 ± 0.35128**ΔΔ▲▲ | 743.442 | 0.0001 |
| Large-dose | 7 | 10.6948 ± 0.30840**ΔΔ▲▲ |  |  |
| Moderate-does | 7 | 15.8423 ± 0.30079**ΔΔ▲▲ |  |  |
| Small-dose | 7 | 13.3003 ± 0.37950**ΔΔ▲▲ |  |  |

Compared with the control group,
*P < 0.05,
**P < 0.01;
compared with the model group,
ΔP < 0.05,
ΔΔP < 0.01;
compared with the Metoprolol group,
▲P < 0.05,
▲▲P < 0.01.

The results revealed that, compared with the control group, the concentrations were all significantly reduced (p<0.01) in the other groups, especially in the model group, that, compared with the model group, the concentrations increased significantly in all treatment groups (p<0.01), and that, compared with the Metoprolol group, the concentrations were a little bit low in the Shengsong Yangxin capsule groups and the three groups treated with the extract.

4. Discussion 4.1 The Physiological Action of $Na^+$—$K^+$-ATPase $Na^+$—$K^+$-ATPase is also called sodium-potassium pump. It is a vital ionic pump on cell membrane. It possesses a large sub-unit involved in hydrolysis of ATP and a small sub-unit, a glucoprotein. The phosphorylation and dephosphorylation lead to a conformational change and result in the change in affinity of $Na^+$ and $K^+$. When a ATP hydrolysis is triggered, an ATPase pumps three sodium ions out of the cell for every two potassium ions pumped in. The process creates the transmembrane gradient and potential, which is the basis of nevermuscle excitement. The increase of concentration of $Na^+$ in the cell or the concentration of $K^+$ outside the cell can activate $Na^+$—$K^+$-ATPase. The transportation of ions is dependent on the process of phosphorylation. A cAMP of ATP was moved to residue aspartic acid, which results in the conformational change.

The physiological significance of $Na^+$—$K^+$-ATPase: 1) maintaining high concentration of potassium in the cell, which is a necessity for cells regular metabolism; 2) maintaining high concentration of sodium outside the cell plays a vital role in maintaining cell normal structure and normal body fluid volume; 3) the unbalanced distribution of ions inside and outside the cell is the basis of biopotential, that is, outward flow of potassium ions creates resting potential and the inward flow of sodium ions generates the action potential; 4) providing energy for other substance active transportation; 5) maintaining pH value in the cell, and providing the power for the exchange of $Na^+$—H.

4.2 The Physiological Action of $Ca^{2+}$-ATPase $Ca^{2+}$-APTase is also called calcium pump. It is located at cell membrane, sarcoplasmic reticulum and endoplasmatic reticulum. The one at cell membrane, that is, plasma membrane calcium pump, decomposes an ATP, then transports a $Ca^{2+}$ outside the cell; the one on sarcoplasmic reticulum and endoplasmatic reticulum, that is, sarcoplasmic reticulum calcium pump, decomposes an ATP and 2 $Ca^{2+}$ are transported into the cell. The mechanism is similar to that of $Na^+$—$K^+$-ATPase, that is, through the process of phosphorylation and dephosphorylation, the transportation of $Ca^{2+}$ is accomplished. $Ca^{2+}$-ATPase consists of a peptide chain. It has 10 transmembrane a helices with N-end and C-end at cytoplasmic side to which ATP and $Ca^{2+}$ bind and it is phosphosite as well. Besides, the C-end in cytoplasm has a domain that can combine with complex of $Ca^{2+}$ and calciumlin (CaM). The domain can inhibit the activity of $Ca^{2+}$-ATPase. When the concentration of $Ca^{2+}$ increases in cytoplasm, more complexes of $Ca^{2+}$-CaM are generated. They can bind to the domain, then cancel the inhibition of the activity of $Ca^{2+}$-ATPase, thus enhancing the its affinity to $Ca^{2+}$, improving transportation efficiency, and speeding up the outward transportation of $Ca^{2+}$. This is a negative feedback mechanism for $Ca^{2+}$ stable status in the cell. At sarcoplasmic reticulum, the $Ca^{2+}$-ATPase possesses a similar regulating mechanism. However, the domain that inhibits its activity is not at C-end, but it is the phosphlamban that is separated from $Ca^{2+}$-ATPase.

The primary function of $Ca^{2+}$-ATPase is to maintain the low level of $Ca^{2+}$ in cytoplasm. This is significant for maintaining the normal physiological function of the cell. The transmembrane gradient of $Ca^{2+}$ is maintained by multiple mechanisms, including the functions of $Ca^{2+}$-ATPase at membrane, sarcoplasmic reticulum and endoplasmatic reticulum, and $Na^+$—$Ca^{2+}$ exchanger. When the concentration of free $Ca^{2+}$ in cytoplasm irreversibly increases for a long time, calcium overload ensues, which intoxicates the cell, and even result in necrosis.

4.3 $Na^+$—$Ca^{2+}$ Exchange Mechanism

The $Na^+$—$Ca^{2+}$ exchanger is a two-way transport system. It transports 3 $Na^+$ into the cell while moves 1 $Ca^{2+}$ out of the cell. Which ion is transported lies on the differences between the concentrations of the $Na^+$ and of the $Ca^{2+}$ inside and outside the cell, and on the membrane potential. During most of the time of resting potential and action potential, $Ca^{2+}$ is transported out of the cell via $Na^+$—$Ca^{2+}$ exchange while a lot of $Na^+$ move in the cell. This generates an inward current and recovers the positive potential in cytoplasm. Its function is to use sodium pump to create the $Na^+$ concentration gradient potential to move $Ca^{2+}$ out off the cell so as to maintain low concentration of $Ca^{2+}$ in the cell. $Na^+$—$Ca^{2+}$ exchange is a key mechanism for cardiac muscles to maintain $Ca^{2+}$ stable status. When action potential repolarization is at the end of phase 3, the $Na^+$—$Ca^{2+}$ exchange mechanism is activated to move out the $Ca^{2+}$, which was once transported inward through L-type Calcium channel. The reversal of the $Na^+$—$Ca^{2+}$ mechanism may induce the inward transportation of $Ca^{2+}$. Therefore, moving calcium inward through L-type calcium channel is the primary trigger signal released by sarcoplasmic reticulum. When myocardial ischemia occurs, the function of $Na^+$—$Ca^{2+}$ exchange is weak, which increases the concentration of $Ca^{2+}$ and results in arrhythmia, the arrest of myocardium, and even necrosis.

4.4 The Influence of the Activities of $Na^+$—$K^+$-ATPase and $Ca^{2+}$ ATPase on Myocardial Ischemia and Arrhythmia When cardiac muscles are ischemic, the aerobic metabolism swiftly switches to anaerobic glycolysis. This exhausts the ATPs in cardiac muscles. The low level of ATP can further induce a series of abnormal metabolism. Relying on ATPs, the activities of $Na^+$—$K^+$-ATPase and $Ca^{2+}$-ATPase slow down, which gives rise to the over lost of $K^+$ and the increase of $Na^+$ in the cell. This further affects $Na^+$—$Ca^{2+}$ exchange and increases the concentration of $Ca^{2+}$ in the cell. The low activity of $Ca^{2+}$-ATPase slows down the transportation of calcium out of the cell. Thus the concentration of $Ca^{2+}$ increases in the cell. The two processes interact and generate the overload of calcium in the cell. The overload of calcium is depolarized via ryanodine receptor and the inward current of $Na^+$—$Ca^{2+}$ exchange, then the $Ca^{2+}$ is released. This is the delayed after depolarization that induces arrhythmia.

4.4.1 The Influence of Low Activity of $Na^+$—$K^+$-ATPase on Myocardial Ischemia and Arrhythmia Located at cell membrane, $Na^+$—$K^+$-ATPase is a pump for energy exchange. Apart from the typical function of ions transportation, it transmits signals from outside into the cell by regulating tyrosine protein phosphorylation. $Na^+$—$K^+$-ATPase can activate Scr tyrosine kinas. It can phosphorate proteins and put them in various signal units. The activated protein kinase cascade includes MAPL, P13/Akt and PKC. Through the signal cascade reaction of Scr/Extracellular signal-regulated kinases ½ (ERK½), the regional combination of SSA412 with $Na^+$—$K^+$-ATPase activates $Na^+$—$K^+$-ATPase. This increases the inward flow of calcium and enhances the contraction of cardiac muscles to protect heart function and correct ischemia. A polyclonal antibody, NKA DR region-specific antibody (DRRSAb), targeting the region of 897DVEDSYGQQWTYEQR911 of the subunit of NKA-α, can increase NKA's activity with dose-response manner and significantly increase the survival rate of the cells in the hearts isolated for 24 hours. When acute MI occurs, myocardial stunning ensures and at the same time the activity of $Na^+$—$K^+$ATPase in membrane slows down conspicuously. The activity of $Na^+$—$K^+$ATPase and the diastolic pressure of left ventricle in the MI group induced by left-anterior-descending-artery ligation and sham operation group were measured at day 3 and 30 respectively, the activity of $Na^+$—$K^+$ATPase and contraction of the cardiac muscles decreases significantly. The decrease of the activity of $Na^+$—$K^+$ATPase can affect the transportation of $Na^+$, $K^+$, and $Ca^{2+}$ via endoplasmatic reticulum and lead to dysfunction of the left ventricle and induce arrhythmia.

Furthermore, during ischemia, $Na^+$—$K^+$-ATPase activity slows down and the $Na^+$ increases in the cell. Thus $Na^+$ overload ensues due to the $Na^+/H^+$ exchange triggered by acidosis. The $Na^+/HCO3$-action prompts to correct the acidosis and the $Na^+$ transportation in gap junctional intercellular communication in cells. This reverses the transportation of the $Na^+$—$Ca^{2+}$ exchanger and the $Na^+$ is moved out of the cell and $Ca^{2+}$ into the cell, which leads to the calcium overload. The calcium overload in diastole results in after depolarization and after contraction related to unstable cell electronic energy. Therefore, the ventricular arrhythmia occurs. After the ischemic heart without ischemic preconditioning is treated with reperfution for 5 minutes, the activity of $Na^+$—$K^+$-ATPase decreases conspicuously. The α1 and α2 subunits in $Na^+$—$K^+$-ATPase are separated from the cell structure, which is consistent with the hydrolysis of calmodulin and α-fordin. The ischemic preconditioning can speed up the recovery of sodium current and promote the activity of $Na^+$—$K^+$ATPase so as to prevent $Na^+$—$K^+$-ATPase separating from the cell. It can also prevent calmodulin and α-fordin from activation and reduce the release of LDH, MI area and damage to the cardiac muscles. This suggested that by increasing the activity of sodium-potassium pump during reperfution, ischemic preconditioning could protect cardiac muscles from damage and reduce the incidence of reperfution-triggered arrhythmia.

4.4.2 The Influence of that the Activity of $Ca^{2+}$-ATPase Decreases on Ischemia and Arrhythmia $Ca^{2+}$-ATPase on sarcoplasmic reticulum plays a vital role in regulating the calcium level and excitation-contraction coupling of myocardium. During diastole, the $Ca^{2+}$-ATPase absorbs the free $Ca^{2+}$ from cytoplasm into sarcoplasmic reticulum. During the contraction of cardiac muscles, sarcoplasmic reticulum releases $Ca^{2+}$ via RyR2 into cytoplasm. They attach to troponins to induce muscle contraction and the cardiac muscle's excitation-contraction coupling is accomplished. When the activity of $Ca^{2+}$-ATPase decreases, retransporting $Ca^{2+}$ is reduced, which leads to intracellular calcium overload. The release of the overload calcium in sarcoplasmic reticulum is done by depolarization though ryanodin receptor and inward current created by $Na^+$—$K^+$ exchange, that is, delayed after depolarization. It is the basis for arrhythmia and might be associated with occurrence and existence of active fibrillation. Besides, the calcium overload in sarcoplasmic reticulum increases the activity of $Na^+$—$Ca^{2+}$ exchange during diastole, which may induce after depolarization and trigger the arrhythmia and even the fetal ventricular arrhythmia.

The activity of $Ca^{2+}$-ATPase at sarcoplasmic reticulum is regulated by phospholamban, a small molecule consisting of 52 amino acids. In non-phosphorylated status, it reduces the sensibility of $Ca^{2+}$-ATPase to $Ca^{2+}$ whereas, in phosphorylated status, it increases the sensibility. However, the phosphorylization of phospholamban may be catalyzed by many enzymes, including calmodulin-dependent protein kinase and c-ATP-dependent kinase-A. A few weeks after model rats' left anterior descending arteries were blocked, the levels of protein and mRNA of $Ca^{2+}$-ATPase at sarcoplasmic reticulum decreased. In left ventricular remodeling after MI, the activity of $Ca^{2+}$-ATPase decreased as well. Besides, the intervention with limited sodium can prevent the sodium accumulation induced by ischemia and reperfution. Moreover, in ischemia, the consumption of ATP resulted in the decrease of the activity of $Ca^{2+}$-ATPase, which decreased electro-chemical potential and promoted the inward flow of $Ca^{2+}$. The ischemic preconditioning can reduce the calcium overload so as to protect cardiac muscles and reduce the incidence of arrhythmia.

4.5 The Effect of the Extract on $Na^+$—$K^+$-ATPase and $Ca^{2+}$-ATPase

The results of the study revealed that after acute MI occurred in rats, their activities of $Na^+$—$K^+$-ATPase and $Ca^{2+}$-ATPase decreased. Treated with the extract, Metoprolol, or Shengsong Yangxin capsule, the activities of $Na^+$—$K^+$ATPase and $Ca^{2+}$-ATPase in the rats increased to various degrees. Moreover, experiment example 1 suggested that the extract was able to reduce the MI area significantly, thus protecting cardiac muscle's function.

As discussed above, during ischemia, the activities of $Na^+$—$K^+$ATPase and $Ca^{2+}$-ATPase slowed down, which caused sodium overload in the cell. By way of $Na^+$—$Ca^{2+}$ exchange, the exchanger reversely transported the ions, thus leading to calcium overload in the cell. It could induce the delayed after depolarization and trigger arrhythmia. However, as the activities of $Na^+$—$K^+$ATPase and $Ca^{2+}$-ATPase increased, the calcium overload could be reduced so as to protect cardiac muscles, maintain stable signals and reduce the incidence of arrhythmia.

Using the extract as pretreatment, its effect was explored on the activities of $Na^+$—$K^+$-ATPase and $Ca^{2+}$-ATPase in ischemic reperfution cardiac muscles. The results revealed, compared with sham operation group after ischemic reperfution injury, the activities of $Na^+$—$K^+$-ATPase and $Ca^{2+}$-ATPase in extract groups decreased significantly; compared with the model group, the activities of $Na^+$—$K^+$-ATPase and $Ca^{2+}$-ATPase in the extract groups increased significantly. This suggested that the pretreatment with the extract could enhance the activities of $Na^+$—$K^+$ATPase and $Ca^{2+}$-ATPase, thus promoting the $Na^+$—$Ca^{2+}$ exchange and reducing calcium overload in the cell, protecting cardiac muscles from damage and reducing the occurrence of arrhythmia.

In sum, the invention stated that, by way of increasing the activities of $Na^+$—$K^+$-ATPase and $Ca^{2+}$-ATPase, the extract could reduce calcium overload in the cell, improve ischemic status, reduce MI area, and reduce the delayed after depolarization so as to decrease the incidence of arrhythmia.

EXPERIMENTAL EXAMPLE 6

1 Materials and Method 1.1.1 Materials
1.1.1 Animals

Healthy Wistar male rats, weight 200 to 220 g, were supplied by Beijing HFK Bioscience Co., Ltd. Serial No.: SCXK Beijing 2009-0007.

1.1.2 Instruments and Equipment

DT-2000 electronic scale was made by Two Brothers Co. Ltd. BS224S electronic scale was made by Sartouris in Germany. Enzyme-labelled meter 352 was manufactured by Labsystems Multiskan in Finland. Micro-plate washer AC8 was made by Thermo Labsystems in Finland. High speed micro-centrifuge TG16W was manufactured in China. Water jacket incubator GNP-9080 was made in China. Bio-Rad electrophoresis meter (constant current and voltage) Powerpac HQ was made in USA. Bio-Rad vertical electrophoresis system MP3 was made in USA. Bio-Rad Semi-dry transfer unit, Trans-Blot SD, was made in USA. Image-Pro Plus Analysis Software 6.0. High speed micro-centrifuge (4° C.) MR23i was manufactured by Thermo in USA. High speed micro-centrifuge (room temperature) 5417C was manufactured by Eppendorf in Germany. UV-VIS spectrophotometer (Biophotometer) was made by Eppendorf in Germany. Microsyringe eppendorf Research plus was made by Eppendorf in Germany. Thermostatic water bath HHW-420 was made in Shanghai, China. Liquid nitrogen tank and potable sample storage tank YDS-30-125 were made in Sichuan, China.

1.1.3 Medicines and Reagents

The extract of Rhizoma Corydalis, yellowish powder, was obtained by conducting the experiment in example 3, Batch no. 1: 201107. One gram of the extract was equivalent to 62.762 grams of crude medicinal; Batch no. 2: 201107. One gram of the extract was equivalent to 65.50218 grams of crude medicinal. Metoprolol, 25 mg/tablet, was supplied by AstraZeneca Pharmaceutical Co. Ltd. Batch no.: 1105031. Shengsong Yangxin capsule, 0.4 g/capsule, was prepared by Hebei Yiling Pharmaceutical Co. Ltd. Batch no. 1104007. Chloral hydrate was supplied by Sinopharm Chemcial Reagent Co. Ltd. Batch no.: 20110210.

Western Blot used acrylamide, bisacrylamide, ponceau, sodium dodecylsulfate, β-mercaptoethanol. Bio-Rat Protein Molecular Weight Marker was made in USA, article no. 161-0374, Batch no. 310007919. Nitrocellulose membrane was made by Millipore in Germany, article no. IPVH00010, Batch no. K1EA1531FK. Light-sensitive film was made by Kodak, USA, article no. XBT-1, Batch no. 020901701. The primary antibody of connexin 43 and phospho-connexin 43 (ser 368) were rabbit ploy-colonal antibody supplied by CST, USA, Batch No. 08/2011. The secondary antibodies were HRP-labeled goat anti-rabbit IgG and HRP-labeled rabbit anti-goat IgG supplied by Beijing Zhongshan Goldenspace Biotechnology Co. Ltd.

Two primary antibodies were used in immunohistochemical test. The connexin 43 rabbit ploy-colonal antibody was supplied by CST, USA, Batch No. 08/2011 and phospho-connexin 43 (ser 368) rabbit ploy-colonal antibody was supplied by Santa Cruz, USA, Batch no. G2011. SP 2-step reagent kit for secondary antibody was supplied by Beijing Zhongshan Goldenspace Biotechnology Co. Ltd., Batch no. K116812C. Anhydrous ethyl alcohol was supplied by Beijing Chemical Works, 2500 ml/bottle, Batch no. 20110808. 95% ethanol was supplied by Beijing Chemical Works, 2500 ml/bottle, Batch no. 20110808. Formalin solution was supplied by Xilong Chemical Corporation, 500 ml/bottle, Batch no. 1110082. Xylene solution was supplied by Beijing Chemical Works, 500 ml/bottle, Batch no. 20110808. Paraffin section (54-56° C.) was supplied by Beijing Beihuakangtai Reagents Co. Ltd., Batch no. 20110428. DAB reagent kit was supplied by Beijing ComWin Biotech Co. Ltd., Batch no. 03911H. Polylysine, strength 25 mg, was supplied by Shanghai Sigma-aldrich Trading Co. Ltd., Batch no. P1399. Microscopic cover glass (24×24 mm) and slide glass (model 7105) were supplied by Beijing Chuanganghuaxin Experimental Instrument Co. Ltd. Stainless steel pressure port, microwave oven, thermostatic waterbath, immunohistochemistry kit, antigen retrieval kit, and microscope.

1.2 Methods 1.2.1 Animal Models Establishment

The rats were fixed the on their back on board and chloral hydrate (3.5%, 10 mg/kg) intraperitoneally administered. Between the rib 4 and 5 on the left side, an open was cut into pleural cavity and the pericardium was torn open, then the heart was extruded by light pressure to the thorax. Two mm beneath left auricle, a ligation was done on left anterior descending artery with surgical suture (USP 0) and the heart was put back to the thorax. The cut open was closed and stitched. Penicillin (up to 80,000 unit) was used for the incision to protect again infection.

1.2.2 Grouping

Eighty-four rats' models were randomly assigned to 6 groups, 14 for each. They were the model group, the Metoprolol group, the Shengsong Yangxin capsule group, the large-dose extract group, the moderate-dose extract group, the small-dose extract group. Two more groups added were the control group of 13 rats and sham operation group of 13 rats. Some rats were dead the next day before intragastrical administration: 1 in the sham operation group, model group, Metoprolol group, Shengsong Yangxin capsule group, large-dose extract group and moderate-dose extract group respectively and 2 in the small-dose extract group.

1.2.3 Medicines Doses and Preparation. See Section 1.2.3 in the Experiment Example 1.

1.2.4 Treatment Administration

Starting from the next day after model establishment, the treatments were all administered intragastrically to the relevant groups accordingly, while the control group, the model group and the sham operation group were intragastrically given normal saline (1 mL/100 g). The treatment course lasted for 7 days.

1.2.5 The Assessment of MI Areas

Two hours after the last treatments were finished, the hearts of the rats were harvested and the residues of blood in the heart chambers were washed with normal saline. Of them, 3 were randomly selected from each group for Western Blot test, the rest were used for immunohistochemical test. For Western Blot test, the MI areas were cut off from ligation position and were instantly frozen with liquid nitrogen; For immunohistochemical test, the left ventricles of the hearts were all cut off with sharp blade and fixed for 24 hour in 10% formalin solution, then labeled with group names respectively.

2 Western Blot Test 2.1 The Reagents Required for Western Blot Test

1) Protein lysis buffer, 50 mmol/LTris.cl (pH 8.0), 150 mmol/L NaCl, 0.025% NaN3, 0.1% SDS, 100 μg/ml PMSF, 1 μg/ml, Aprotinin, 0.5% sodium deoxycholate, and 0.1% NP-40.

2) Solution A (30% acrylamide stock solution). Taking acrylamide 29.0 g, N-methylenebisacrylamide 1 g, then adding 1120 up to 100 ml. The solution was stored away from light in brown flask, and the pH was adjusted to less than 7.0.

Solution B (spacer gel buffer). Taking 6 g Tris and dissolving it with 40 ml H2O, and using 1 mol/L (48 ml) to adjust the solution's pH value to 6.8 and diluting it up to 100 ml with water. This was the 0.5 mol/L Tris-HCl buffer solution at pH 6.8. It was filtered and stored at 4° C.

Solution C (separating gel buffer). Taking 36.6 g Tris and mixing it with 48 ml 1 mol/L HCL, diluting the solution up to 100 ml with water. This was the 3 mol/L Tris-HCL buffer at pH 8.8, and filtering it then storing it at 4° C.

Solution D (electrophoresic buffer stock solution). Taking 30.3 g Tris, 114 g glycine and 10 g DSD, dissolving them with water up to 100 ml. This was the glycine electrophoresic buffer stock solution. It should be diluted 10 times before it could be used.

Solution E. Taking 1 g DSD and dissolving it with 10 ml water. This was the 10% DSD solution.

Solution F. The 10% ammonium persulfate solution was prepared within a week before it was used.

Solution G. Tetramethyl ethylenediamine solution.

Solution H (sampling buffer). It was prepared with 8 ml solution B, 6.4 ml grycerine, 12.8 ml solution E, 3.2 ml 2-Mercaptoethanol, 1.6 ml 0.05% bromophenol blue solution and 32 ml distilled water. They were mixed evenly.

Solution I (10% SDS-PAGE separating gel). 6.65 ml 30% crylamide stock solution, 5 ml separating get buffer, 8.25 ml deionized water, 150 μl 10% ammonium persulfate solution, and 20 μl tetramethyl ethylenediamine solution. Total volume was 20 ml mixed evenly and used immediately.

Solution J (5% spacer gel). It was prepared with 2.1 ml crylamide stock solution, 3.76 ml spacer gel buffer, 9 ml deionized water, 45 μl 10% ammonium persulfate solution, 15 μl tetramethyl ethylenediamine solution. Total volume was 15 ml mixed evenly and used immediately.

3) Nitrocellulose membrane 0.45 μm was supplied by Millipore Co. Ltd, USA.

4) Transfer buffer. Taking 3 g Tris base, 1 g SDS and 14.4 g glycine and dissolving them with 200 ml methanol, and then diluting it with distilled water up to 1 L.

5) Coomassie brilliant blue G250 solution (stain fixation solution). It was prepared by taking 1.25 coomassie brilliant blue G250, and mixing it with 230 ml methanol, 230 ml distilled water, and 40 ml glacial acetic acid.

6) Destaining solution. It was prepared by mixing 230 ml methanol, 230 ml distilled water, and 40 ml glacial acetic acid.

7) Blocking buffer. It was prepared by dissolving 5% dry skim milk, 0.01% antifoaming agent and 0.025% NaH3 with TBS-T buffer.

8) 5×TBS buffer. Taking 12.11 g Tris base and 40 g NaCL, dissolving them in double-distilled water, and adding HCL to adjust the pH to 7.6, then diluting it with double-distilled water up to 1 L.
9) TBS-T solution. The TBS that contained 0.1% Tween-20.
10) Protein maker was supplied by MBI, USA.
11) Developing solution and fixing solution were supplied by China Lucky Group Corporation.

2.2 Western Blot Testing Procedure 2.2.1 Tissue Protein Extracted and Determination Taking out the tissue for nitrogen liquid, putting it into a precooling mortar and adding nitrogen liquid to it and quickly grinding it, then putting the powder in precooling EP tubes, adding protein lysis solution 50 μl into each tube, freezing them for 20 minutes, and conducting centrifuge with 10000 r/min at 4° C. for 10 minutes, taking the supermatant and putting it in precooling EP tubes, letting precipitated and discarding them. After determining the protein with Bradford method, adding the same volume of 2×SDS sampling buffer into the remained protein, then boiling them in water for 5 minutes.

2.2.2 Gel and Sample Preparation

Preparing 10% SDS-PAGE separating gel solution, mixing it evenly then injecting it to the glass plate, then vertically placing and then tilting the plate to get rid of the separated water, absorbing away the remained water on the gel with absorbent paper; inserting the comb and slowly adding 5% concentrated gel, letting stand at room temperature. After the gel completely solidified, removing the edging at the bottom part, placing the well-prepared glass plate with solidified gel on eletrophorator. Adding electrophoresic buffer and making sure the buffer cover the gel completely, removing the comb carefully, and washing the sample-added holes several time with eletrophorestic buffer; Taking 40 μg total protein sample and the maker for protein molecular weight, and adding 5× sample buffer according to the ratio of 1:4; balancing added sample's volume with 1× sample buffer and boiling them in water for 5 minutes to denaturing the protein; Putting the well-treated samples in the holes of adding concentrated gel according to the predetermined order.

2.2.2 Electrophoresis

Supplying the power with initial voltage of 80 v and increasing the voltage to 100 v after bromophenol blue entering separating gel until bromophenol blue leaving the separating gel.

2.2.4 Electrotransfer and Membrane Blocking

Cutting 6 filter sheets to fit the measurement of the gel, and one polyvinylidene fluoride (PDVF) membrane and Wetting filter sheets for 15 minute in transfer buffer, transferring the protein with semi-dry electrotransfer for 90 minutes with constant current of 30 mA. After finishing the transfer, taking out the PDVF membrane, marking the membrane's direction and blocking the membrane with 5% TBS-T skim milk, and then shaking them at room temperature for 60 minutes.

2.2.5 Reaction of Antigen and Antibody, and Image Fixation

After finishing the block, washing the membrane with TBS-T for 10 minutes 3 times, putting the membrane into a hybridizatio bag and adding the antibodies of connexin 43 and p-connexin 43 all diluted with buffer (1:2000), and sealed the bag, then incubating it at 4° C. overnight; washing the membrane with TBS-T for 10 minute 3 times, then putting the membrane in another hybridization bag, adding the HRP-labeled secondary antibodies of connexin 43 and p-connexin 43 (1:2000), and shaking it for 60 minutes, then washing it with TBS-T for 10 minutes 3 times; putting PVDF membrane in ECL mix and incubating it while shaking it for 5 minutes at room temperature, covering the whole membrane with ECL mix, at least 0.125 ml/cm2, then clipping the membrane with tongs, vertically tipping it on the absorbent paper to absorb away the remained water, putting the membrane between the two films ensuring no bubbles between them. Letting the side faced up of the membrane absorbing the protein, and put it in the x-ray box, putting x-ray sensitive film, letting it exposed to light for a few minute. Putting the exposed film in the developing solution until sharp images appeared, then putting the film in water to wash it for a while, and then putting the film into the fixation solution. Washing the film again, letting it dried and scanning it, and analyzing the gray degree of the electrophoresis bands. Repeating the tests 3 times.

3. Immunohistochemical Test and HE Staining 3.1 The Reagents Required for Immunohistochemical Test
1) pH 7.2 0.01 PBS Buffer
   Solution A. 0.2 mol/L $NaH_2PO_4$ and 27.6 g $NaH_2PO_4.H_2O$ were dissolved with double-distilled $H_2O$ and the solution were diluted up to 1000 ml.
   Solution B. 0.2 mol/L $NaH_2PO_4$ and 53.6 g $NaH_2PO_4.7H_2O$ (or 71.6 g $Na_2HPO_4.12H_2O$ or 35.6 g $Na_2HPO_4.2H_2O$) were dissolved with double-distilled $H_2O$. The solution were diluted up to 1000 ml.
   When using the two solutions, taking 28 ml solution A, 72 ml solution B and 118 g NaCl, then adding 1900 ml $H_2O$ to them.
2) Antigen Retrieval Solution 0.02 Mol/L pH 6.0
   Solution A.0.1M citrate solution (21.01 g $C_6H_8O.7H_2O$ were dissolved with double-distilled $H_2O$, the solution was diluted up to 1000 ml).
   Solution B.0.1M sodium citrate solution (29.41 g $C_6H_5O_7.3H_2O$ were dissolved with double-distilled $H_2O$ and the solution was diluted up to 1000 ml).
   When using the two solutions, taking 18 ml solution A, 82 ml solution B and mixing them, then adding $H_2O$ to dilute the solution up to 1000 ml.
   0.01% Triton-100 was prepared with 100% Triton-100.
   The solution of 3% $H_2O_2-CH_3OH$ was prepared with 30% $H_2O_2$ and 80% methanol solution using the ratio of 1:9.
5) Mounting Media was Neutral Balsam.

4 Data Analysis

Data were processed with SPSS 16.0. Chi-square or rank test and ANOVA were performed. $P<0.05$ was the significant level.

5 Results 5.1 The Outcomes of Western Blot Test
5.1.1 The Outcomes of Connexin 43

TABLE 5

| The gray degree of connexin 43 ($\bar{x} \pm SD$) | | | | |
|---|---|---|---|---|
| Group | n | Gray degree of Connexin 43 | F | P-value |
| Control | 3 | 0.8629 ± 0.02288 | 13.49 | 0.0001 |
| Shame operation | 3 | 0.9484 ± 0.10929 | | |
| model | 3 | 0.2453 ± 0.11019** | | |
| Metoprolol | 3 | 0.5443 ± 0.15226**ΔΔ | | |
| Shengsong Yangxin capsule | 3 | 0.5581 ± 0.18178**ΔΔ | | |
| Large-dose extract | 3 | 0.3728 ± 0.03228** | | |

TABLE 5-continued

The gray degree of connexin 43 ($\bar{x} \pm SD$)

| Group | n | Gray degree of Connexin 43 | F | P-value |
|---|---|---|---|---|
| Moderate-dose extract | 3 | 0.6057 ± 0.08018*▲▲ | | |
| Small-dose extract | 3 | 0.5063 ± 0.08884**▲ | | |

Compared with the control group,
*P < 0.05,
**P < 0.01;
compared with the model group,
ΔP < 0.05,
ΔΔP < 0.01;
compared with the Metoprolol group,
▲P < 0.05,
▲▲P < 0.01;
compared with the Shengsong Yangxin capsule group,
★P < 0.05,
★★P < 0.01.

The results revealed that, compared with the control group, the protein of connexin 43 were significantly reduced in model group and all treatment groups (p<0.05); compared with the model group, the protein of connexin 43 were significantly increased in all treatment groups except the large-dose extract group (p<0.05); compared with the Metoprolol group, the protein of connexin 43 were insignificantly different from that in the Shengsong Yangxin capsule group, large-dose extract group, the moderate-dose extract group, or the small-dose extract group. However there was a trend that as the extract dose increased, the protein of connexin 43 increased, which showed a trend that it might surpass the Metoprolol group.

5.1.2 The Outcomes of Phosphor-Connexin 43

TABLE 6

The gray degrees of phospho-connexin 43 ($\bar{x} \pm SD$)

| Group | n | Gray degree of Connexin43 | F | P-value |
|---|---|---|---|---|
| Control | 3 | 0.9443 ± 0.05676 | 4.760 | 0.005 |
| Sham operation | 3 | 1.0727 ± 0.19626 | | |
| Model | 3 | 0.2268 ± 0.08750** | | |
| Metoprolol | 3 | 0.6830 ± 0.26236Δ | | |
| Shengsong Yangxin capsule | 3 | 0.5906 ± 0.21438 | | |
| Large-dose extract | 3 | 0.4901 ± 0.22870* | | |
| Moderate-dose extract | 3 | 0.8253 ± 0.29672ΔΔ | | |
| Small-dose extract | 3 | 0.4900 ± 0.27663* | | |

Compared with the control group,
*P < 0.05,
**P < 0.01;
compared with the model group,
ΔP < 0.05,
ΔΔP < 0.01;
compared with the Metoprolol group,
▲P < 0.05,
▲▲P < 0.01;
compared with the Shengsong Yangxin capsule group,
★P < 0.05,
★★P < 0.01.

The results showed that, compared with the control group, the protein of phosphor-connexin 43 in the model group significantly decreased (p<0.05), that although the protein in the large-dose extract group decreased, it was not significant (p>0.05), and that the protein in the rest of treatment groups decreased significantly (p<0.05). The results also revealed that, compared with the model group, the protein significantly increased in the Metoprolol group and moderate-dose extract group (p<0.05), and the protein in the rest of treatment groups increased insignificantly (p<0.05), The results also displayed that, the protein in all treatment groups were not significantly different from that of the Metoprolol group (p>0.05), but the moderate-dose group showed the trend to surpass the Metoprolol group.

5.2 The Results of Immunohistochemical Test
5.2.1 The Outcomes of Immunohistochemical Expression of Connexin 43

TABLE 7

The expression areas of connexin 43 and IOD ($\bar{x} \pm SD$)

| Group | n | Area | IOD |
|---|---|---|---|
| Control | 10 | 53739.9200 ± 8211.98879 | 15104.1623 ± 2601.2000 |
| Sham operation | 9 | 32946.6667 ± 7080.3686** | 8681.2899 ± 2098.95456** |
| Model | 10 | 1470.2400 ± 974.92195** | 361.9282 ± 249.38330** |
| Meoprolol | 10 | 17723.1800 ± 6671.83472ΔΔ | 4535.0243 ± 1742.67121ΔΔ |
| hengsong Yangxin capsule | 10 | 17498.6800 ± 6437.29864ΔΔ | 4597.4566 ± 1818.08202ΔΔ |
| Large-dose extract | 10 | 16758.6600 ± 3415.47214ΔΔ | 4280.7530 ± 947.73916ΔΔ |
| Moderate-dose extract | 10 | 33285.5667 ± 9406.21647ΔΔ▲▲★★ | 9218.6902 ± 2839.33530ΔΔ▲▲★★ |
| Small-dose extract | 9 | 16548.7556 ± 7990.49798ΔΔ | 6391.4570 ± 4668.13667ΔΔ |
| Welch | | 115.04 | 97.204 |
| P | | <.0001 | <.0001 |

Compared with the control group,
*P < 0.05,
**P < 0.01;
compared with the model group,
ΔP < 0.05,
ΔΔP < 0.01;
compared with the Metoprolol group,
▲P < 0.05,
▲▲P < 0.01;
compared with the Shengsong Yangxin capsule group,
★P < 0.05,
★★P < 0.01.

The results showed that, compared with the control group, the expression areas and IOD values of connexin 43 significantly decreased in other groups (p<0.01), especially in the model group which showed the largest decrease in connexin 43 expression. The results also revealed that, compared with the model group, the connexin 43 expression increased in all treatment groups (p<0.01), especially in the moderate-dose extract group. The results also displayed that, compared with the Metoprolol group, the connexin 43 expression increased significantly in the moderate-dose extract group (p<0.01), and that there was no significant difference in the rest of treatment groups (p>0.05). The results also revealed that, compared with the Shengsong Yangxin capsule group, the connexin 43 expression increased significantly in the moderate-dose extract group (p<0.01), and that on significant difference (p>0.05) was found in the large-dose extract group, small-dose extract group, and the Shengsong Yangxin capsule group.

5.2.2 The Outcomes of Immunohistochemical Expression of Phosphor-Connexin 43

TABLE 8

The expression areas of phospho-connexin 43 and IOD values ($\bar{x} \pm SD$)

| Group | n | Area | IOD |
|---|---|---|---|
| Control | 10 | 33936.3200 ± 12892.12362 | 6954.9538 ± 2888.33033 |
| Sham operation | 9 | 27656.3333 ± 6366.42470* | 6650.7868 ± 976.93702 |
| Model | 10 | 1727.720 ± 700.66938** | 345.3192 ± 174.94916** |
| Meoprolol | 10 | 13283.8000 ± 8070.47849ΔΔ | 2686.5321 ± 1724.68155ΔΔ |
| hengsong Yangxin capsule | 10 | 8549.600 ± 3136.84524Δ | 1652.4931 ± 726.52637 |
| Large-dose extract | 10 | 12076.380 ± 5462.37090ΔΔ | 2292.0587 ± 914.03147ΔΔ |
| Moderate-dose extract | 10 | 12503.1133 ± 4809.51552ΔΔ | 2791.7334 ± 1631.29058ΔΔ |
| Small-dose extract | 9 | 8296.4222 ± 1663.44896Δ | 2078.0578 ± 907.32972Δ |
| Welch | | 52.947 | 64.675 |
| P | | <.0001 | <.0001 |

Compared with the control group,
*$P < 0.05$,
**$P < 0.01$;
compared with the model group,
Δ$P < 0.05$,
ΔΔ$P < 0.01$;
compared with the Metoprolol group,
▲$P < 0.05$,
▲▲$P < 0.01$;
compared with the Shengsong Yangxin capsule group,
★$P < 0.05$,
★★$P < 0.01$.

The results revealed that, compared with the control group, the expression areas of phosphor-connexin 43 and the IOD values decreased significantly in the other groups (p<0.01), especially in the model group. The results also showed that, compared with the model group, the increase in the expression area of phosphor-connexin 43 was not significant in the Shengsong Yangxin capsule group (p>0.05) but significant in the rest of treatment groups (p<0.05), especially in the moderate-dose extract group. The results also displayed that the expression area in the Metoprolol group was insignificantly different from those in the large-dose, moderate-dose, and small-dose extract groups (p>0.05).

6 Discussion

The study used Western Blot test to assess the amount of protein. The outcomes showed the expression level of CX43-s368 (Ps368-CX43). Compared with the control group and sham operation group, the expression significantly decreased in the model group while increased significantly in all treatment groups. Likewise, the outcomes of immunohistochemical test showed that, compared to the control group, the expression area of Ps368-CX43 and IOD values significantly decreased in the model group whereas they increased variously in all treatment groups. In the model group, the peripheralization appeared in the expression of Ps368-CX43. However, the peripheralization was improved in all treatment groups. The extract was able to improve the CX43 phophorylation in myocardium, reduce the permeability between cells, lessen the flow of harmful substances among cells, ameliorate the inhomogeneous distribution of CX43, better electron coupling, reduce ML area, correct the ischemia, and reduce the incidence of arrhythmia.

In sum, this invention elaborated that the extract could lessen MI area and correct myocardial ischemia. The extract specified by the invention was able to enhance the activities of $Na^+$—$K^+$-ATPase and $Ca^{2+}$-ATPase in myocardium, boost $Na^+$—$Ca^{2+}$ exchange, decrease calcium overload, protect ischemic myocardium from damage, reduced the occurrence of delayed after depolarization, and decrease the incidence of arrhythmia. The extract was also able to increase the protein level of CX43 and P-CX43 S368 in the myocardium after ischemia, to reduce the CX43 periferalization, decrease the permeability between cells, reduce the flow of harmful substances, ameliorate the inhomogeneous distribution of CX43 and P-CX43 S368, better the electron coupling, correct the ischemia, and reduce the incidence of arrhythmia.

Specific Embodiments

Example 1

Corydalis crude powder 100 g, is extracted by 70% ethanol 800 ml in 2 times, combined filtrate, concentrated under reduced pressure to a fluidextract of the relative density of 0.3 g/mL; take the D101 resin processed, and the fluidextract prepared is loaded in the resin column, with the flow rate of 0.4 mL/min, impurity of deionized water, with the flow rate of 0.4 mL/min, 80% ethanol elution 8 times volume, flow rate 0.6 mL/min, and concentrate to Corydalis extract dry paste.

Example 2

Corydalis crude powder 100 g, is extracted by 70% ethanol 700 ml in 3 times, combined filtrate, concentrated under reduced pressure to a fluidextract of the relative density of 0.5 g/mL; take the D101 resin processed, and the fluidextract prepared is loaded in the resin column, with the flow rate of 0.2 mL/min, impurity of deionized water, with the flow rate of 0.5 mL/min, 60% ethanol elution, flow rate 0.8 mL/min, and concentrate to Corydalis extract dry paste.

Example 3

Corydalis crude powder 100 g, is extracted by 70% ethanol 800 ml in 2 times, combined filtrate, concentrated under reduced pressure to a fluidextract of the relative density of 0.3 g/mL; take the D101 resin processed, with the diameter to height ratio of 1:7, and the sample solution of the fluidextracts is adjusted pH 2 to dissolving the precipitate, the fluidextract prepared is loaded in the resin column, with the flow rate of 0.4 mL/min, impurity of deionized water, with the flow rate of 0.4 mL/min, 80% ethanol elution 8 times volume, flow rate 0.6 mL/min, and recover ethanol, concentrate to Corydalis extract dry paste. According to the conventional method of adding conventional accessories, Corydalis dry paste is made into dripping pills.

Example 4

Corydalis crude powder 100 g, is extracted by 70% ethanol 700 ml in 3 times, combined filtrate, concentrated under reduced pressure to a fluidextract of the relative density of 0.5 g/mL; take the D101 resin processed, with the diameter to height ratio of 1:8, and the sample solution of the fluidextracts is adjusted pH 1.5 to dissolving the precipitate, the fluidextract prepared is loaded in the resin column, with the flow rate of 0.2 mL/min, impurity of deionized water, with the flow rate of 0.5 mL/min, 60% ethanol elution, flow rate 0.8 mL/min, and concentrate to Corydalis extract dry paste. According to the conventional method of adding conventional accessories, Corydalis dry paste is made into capsules.

Example 5

Corydalis crude powder 100 g, is extracted by 80% ethanol 1000 ml in 2 times, combined filtrate, concentrated under reduced pressure to a fluidextract of the relative density of 0.3 g/mL; take the D101 resin processed, and the fluidextract prepared is loaded in the resin column, with the flow rate of 0.4 mL/min, impurity of deionized water, with the flow rate of 0.4 mL/min, 80% ethanol elution 8 times volume, flow rate 0.6 mL/min, and recover ethanol, concentrate to Corydalis extract dry paste. According to the conventional method of adding conventional accessories, Corydalis dry paste is made into tablets.

Example 6

Corydalis crude powder 100 g, is extracted by 70% ethanol 700 ml in 3 times, combined filtrate, concentrated under reduced pressure to a fluidextract of the relative density of 0.5 g/mL; take the D101 resin processed, and the fluidextract prepared is loaded in the resin column, with the flow rate of 0.2 mL/min, impurity of deionized water, with the flow rate of 0.5 mL/min, 60% ethanol elution, flow rate 0.8 mL/min, and concentrate to Corydalis extract dry paste. According to the conventional method of adding conventional accessories, Corydalis dry paste is made into the oral liquid preparation.

Example 7

Corydalis crude powder 100 g, is extracted by 70% ethanol 800 ml in 2 times, combined filtrate, concentrated under reduced pressure to a fluidextract of the relative density of 0.3 g/mL; take the D101 resin processed, with the diameter to height ratio of 1:7, and the sample solution of the fluidextracts is adjusted pH 2 to dissolving the precipitate, the fluidextract prepared is loaded in the resin column, with the flow rate of 0.4 mL/min, impurity of deionized water, with the flow rate of 0.4 mL/min, 80% ethanol elution 8 times volume, flow rate 0.6 mL/min, and recover ethanol, concentrate to Corydalis extract dry paste. According to the conventional method of adding conventional accessories, Corydalis dry paste is made into granules.

Example 8

Corydalis crude powder 100 g, is extracted by 70% ethanol 700 ml in 3 times, combined filtrate, concentrated under reduced pressure to a fluidextract of the relative density of 0.5 g/mL; take the D101 resin processed, with the diameter to height ratio of 1:8, and the sample solution of the fluidextracts is adjusted pH 1.5 to dissolving the precipitate, the fluidextract prepared is loaded in the resin column, with the flow rate of 0.2 mL/min, impurity of deionized water, with the flow rate of 0.5 mL/min, 60% ethanol elution, flow rate 0.8 mL/min, and concentrate to Corydalis extract dry paste. According to the conventional method of adding conventional accessories, Corydalis dry paste is made into the injection.

The invention claimed is:

1. A method of preparing a Corydalis extract for anti-tachyarrhythmia treatment, the method comprising:
    extracting Corydalis crude powder, 100 parts by weight, in 60-80% ethanol, 600-1000 parts by volume, 1-3 times and combining the extracted portions to form a filtrate;
    concentrating the filtrate under reduced pressure to form a fluidextract of a relative density of 0.2-0.5 g/mL;
    passing the fluidextract column including a D101 resin at a flow rate of 0.2-0.5 mL/min;
    washing the fluidextract with deionized water at a flow rate of 0.2-0.5 mL/min to remove impurities;
    eluting the fluidextract with 60-90% ethanol elution at a flow rate of 0.4-0.8 mL/min; and
    concentrating the fluidextract to obtain a Corydalis extract dry paste.

2. The method according to claim 1, wherein:
    the Corydalis crude powder, 100 parts by weight, is extracted in 70% ethanol, 800 parts by volume, 2 times;
    the filtrate is concentrated under reduced pressure to form a fluidextract of relative density of 0.3/mL;
    the fluidextract is passed through the resin column including the D101 resin at a flow rate of 0.4 mL/min;
    the fluidextract is washed with deionized water at a flow rate of 0.4 mL/min to remove impurities; and
    the fluidextract is eluted with 80% ethanol elution at 8 times volume and a flow rate of 0.6 mL/min.

3. The method according to claim 1, wherein the diameter to height ratio of the D101 resin is 1:4-8.

4. The method according to claim 3, wherein the diameter to height ratio of the D101 resin is 1:7.

5. The method according to claim 1, wherein the pH of the fluidextract after passing through the resin column is adjusted to 1-2.

6. The method according to claim 3, wherein the pH of the fluidextract after passing through the resin column is adjusted to 1-2.

7. The method according to claim 5, wherein the pH is adjusted to 1.5.

8. The method according to claim 6, wherein the pH is adjusted to 1.5.

9. The method according to claim 1, further comprising formulating the Corydalis dry paste into a pill, capsule, granule, tablet, oral liquid or injectable.

10. The method according to claim 3, further comprising formulating the Corydalis extract dry paste into a pill, capsule, granule, tablet, oral liquid or injectable.

11. The method according to claim 5, further comprising formulating the Corydalis extract dry paste into a pill, capsule, granule, tablet, oral liquid or injectable.

* * * * *